(12) United States Patent
Steinmetzer et al.

(10) Patent No.: US 8,921,319 B2
(45) Date of Patent: Dec. 30, 2014

(54) SERINE PROTEASE INHIBITORS

(75) Inventors: Torsten Steinmetzer, Jena (DE); Sebastian Martin Saupe, Kaltennordheim (DE)

(73) Assignee: The Medicines Company (Leipzig) GmbH, Leipzig (DE)

(*) Notice: Subject to any disclaimer, the term of this patent is extended or adjusted under 35 U.S.C. 154(b) by 97 days.

(21) Appl. No.: 13/808,524

(22) PCT Filed: Jul. 5, 2011

(86) PCT No.: PCT/IB2011/002279
§ 371 (c)(1), (2), (4) Date: Jun. 27, 2013

(87) PCT Pub. No.: WO2012/004678
PCT Pub. Date: Jan. 12, 2012

(65) Prior Publication Data
US 2013/0267467 A1  Oct. 10, 2013

Related U.S. Application Data

(60) Provisional application No. 61/362,127, filed on Jul. 7, 2010.

(51) Int. Cl.
| | |
|---|---|
| A61K 38/05 | (2006.01) |
| C07K 5/037 | (2006.01) |
| C07K 5/062 | (2006.01) |
| C07K 5/065 | (2006.01) |
| C07K 5/078 | (2006.01) |
| C07D 487/18 | (2006.01) |
| C07D 273/01 | (2006.01) |
| C07D 255/04 | (2006.01) |
| C07K 5/06 | (2006.01) |
| C07D 487/08 | (2006.01) |
| C07D 213/56 | (2006.01) |

(52) U.S. Cl.
CPC .............. *C07K 5/06* (2013.01); *C07D 487/18* (2013.01); *C07D 273/01* (2013.01); *C07D 255/04* (2013.01); *C07K 5/06078* (2013.01); *C07D 487/08* (2013.01); *C07D 213/56* (2013.01)
USPC ...... 514/13.6; 514/14.2; 514/21.91; 540/456; 540/460; 544/350; 546/117; 548/258

(58) Field of Classification Search
None
See application file for complete search history.

(56) References Cited

U.S. PATENT DOCUMENTS

| | | | |
|---|---|---|---|
| 6,831,196 B2 | 12/2004 | Sturzebecher et al. |
| 6,841,701 B2 | 1/2005 | Sturzebecher et al. |
| 7,772,251 B2 | 8/2010 | Sturzebecher et al. |
| 7,838,560 B2 | 11/2010 | Sturzebecher et al. |
| 8,124,587 B2 | 2/2012 | Steinmetzer et al. |
| 8,207,378 B2 | 6/2012 | Steinmetzer et al. |
| 2006/0148901 A1 | 7/2006 | Sturzebecher et al. |
| 2007/0066539 A1 | 3/2007 | Sturzebecher et al. |
| 2011/0002992 A1 | 1/2011 | Sturzebecher et al. |
| 2011/0065799 A1 | 3/2011 | Sturzebecher et al. |
| 2012/0225913 A1 | 9/2012 | Steinmetzer et al. |
| 2012/0252743 A1 | 10/2012 | Herold et al. |

FOREIGN PATENT DOCUMENTS

| | | |
|---|---|---|
| WO | WO-2000-058346 A1 | 10/2000 |
| WO | WO-2003-070229 A2 | 8/2003 |
| WO | WO-2007-085461 A2 | 8/2007 |
| WO | WO-2008-049595 A1 | 5/2008 |
| WO | WO-2012-083436 A1 | 6/2012 |

OTHER PUBLICATIONS

International Search Report and Written Opinion for WO2012/004678 issued Jan. 18, 2012.

*Primary Examiner* — Jeffrey E Russel
(74) *Attorney, Agent, or Firm* — Clark & Elbing LLP

(57) ABSTRACT

The invention provides methods of making and using compounds of the formula shown, which are inhibitors of human plasmin and plasma kallikrein. (Formula I) The compounds are useful for the prevention of blood loss, and as components of fibrin adhesives.

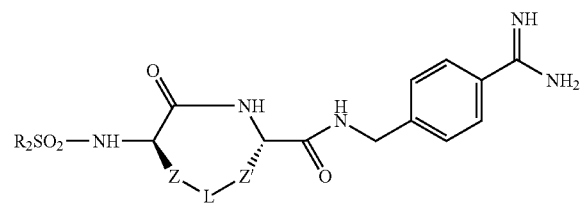

13 Claims, No Drawings

SERINE PROTEASE INHIBITORS

CROSS REFERENCE TO RELEATED APPLICATIONS

This application is the U.S. National Stage of International Application No. PCT/IB2011/002279, filed Jul. 5, 2011, which claims benefit of U.S. Provisional Patent Application No. 61/362,127, filed Jul. 7, 2010, each of which is hereby incorporated by reference in its entirety.

FIELD OF THE INVENTION

The invention relates to the fields of organic chemistry, serine proteases (particularly plasmin and plasma kallikrein), hemostasis, and fibrinolysis.

BACKGROUND OF THE INVENTION

Plasmin (EC 3.4.21.7, fibrinolysin) is a trypsin-like serine protease which effects protein cleavage at arginine or lysine residues; its principal substrates are fibrin and extracellular matrix (ECM) proteins like fibronectin. Other plasmin substrates include various proteins of the basal membrane, for example, laminin and type IV collagen, and zymogens such as the proforms of urokinase and matrix metalloprotceases. In blood, plasmin is responsible in particular for fibrinolysis, as it cleaves fibrin into soluble fragments. Plasmin is activated by cleavage from its precursor zymogen, plasminogen, by the action of plasminogen activators, principally serine proteases such as urokinase, tPA, and plasma kallikrein (EC 3.4.21.34; kininogenin, PK).

Endogenous plasmin inhibitors such as $\alpha_2$-macroglobulin and $\alpha_2$-antiplasmin, by moderating the anticoagulant effects of plasminogen activators, play key roles in regulating fibrinolysis. Certain pathological conditions (hyperplasminemias) are characterized by dysregulation of plasmin and spontaneous activation of fibrinolysis. The resulting degradation of wound-closing fibrin is exacerbated by the anticoagulant properties of the fibrinogen degradation products, leading to a serious impairment of hemostasis.

Antifibrinolytic drugs are used clinically to treat such conditions; among the commonly used agents are synthetic amino-substituted carboxylic acids such as p-aminomethyl-benzoic acid, s-aminocaproic acid, and trans-4-(aminomethyl)-cyclohexanecarboxylic acid (tranexamic acid). These compounds block the binding of plasminogen to fibrin, and thus inhibit the generation of plasmin, but they are not direct inhibitors of plasmin and do not inhibit the activity of already-formed plasmin. A direct antifibrinolytic is aprotinin (TRASYLOL™, Bayer AG, Leverkusen), a 58 amino acid polypeptide obtained from bovine lung. Aprotinin inhibits plasmin with an inhibition constant of 1 nM, but is relatively nonspecific: it effectively inhibits trypsin ($K_i$=0.1 nM), plasma kallikrein ($K_i$=30 nM) and, to a lesser extent, a variety of other enzymes.

The principal use of aprotinin was for reduction of blood loss, especially in cardiac surgical procedures with cardiopulmonary bypass (CPB), where it distinctly reduced the need for perioperative blood transfusions (Sodha et al., *Expert Rev. Cardiovasc. Ther.*, 4, 151-160, 2006). Aprotinin was also employed to inhibit blood loss in other operations, for example in organ transplants; it is also used in conjunction with fibrin adhesives.

The use of aprotinin has several disadvantages. Since it is isolated from bovine organs, there is in principle the risk of pathogenic contamination and allergic reactions. The risk of anaphylactic shock is relatively low with the first administration of aprotinin (<0.1%), but increases on repeated administration within 200 days to 4-5%. It has been reported that administration of aprotinin, in direct comparison with ε-aminocaproic acid or tranexamic acid, induces an increased number of side effects (Mangano et al., *New Engl. J. Med.*, 354, 353-365, 2006). Administration of aprotinin led to a doubling of the number of cases of kidney damage requiring dialysis, and the incidence of myocardial infarction and apoplectic stroke was increased in comparison with the control groups. After the Blood Conservation Using Antifibrinolytics in a Randomized Trial (BART) study had shown an increased risk of mortality associated with aprotinin use compared to lysine analogues in high-risk cardiac surgery patients (Fergusson et al., *New Engl. J. Med.*, 358, 2319-2331, 2008), the drug was withdrawn from the market.

A number of synthetic inhibitors of plasmin have been disclosed. Sanders and Seto, *J. Med. Chem.*, 42, 2969-2976, 1999, have described 4-hetero cyclohexanone derivatives with relatively weak activity, with inhibition constants of ≥50 µM for plasmin. Xue and Seto, *J. Med. Chem.*, 48, 6908-6917, 2005, have reported on peptidic cyclohexanone derivatives with $IC_{50}$ values≥2 µM, but no further development has been reported. Okada (Okada et al., *Chem. Pharm. Bull.*, 48, 1964-1972, 2000; Okada et al., *Bioorg. Med. Chem. Lett.*, 10, 2217-2221, 2000) and Tsuda (Tsuda et al., *Chem. Pharm. Bull.*, 49, 1457-1463, 2001) described derivatives of 4-aminomethyl-cyclohexanoic acid which inhibit plasmin with $IC_{50}$ values ≥0.1 µM, but clinical use of these inhibitors has not been reported. Potent plasmin inhibitors have recently been described (WO 2008/049595; Dietrich et al., *Anesthesiology*, 110, 123-130, 2009), but these compounds have limited selectivity and inhibit other trypsin-like serine proteases.

Stürzebecher et al. have described a series of N-terminal sulfonylated benzamidine peptidomimetics having various effects on serine proteases. Included within this class are factor Xa inhibitors, useful as anticoagulants and antithrombotics (U.S. Pat. No. 6,841,701); urokinase inhibitors, useful as tumor suppressors (US Pat. Application Publication No. 2005/0176993, U.S. Pat. No. 6,624,169); inhibitors of plasma kallikrein (PK), factor XIa and factor XIIa, useful as anticoagulants and antithrombotics (US Pat. Application Publication No. 2006/0148901); and matriptase inhibitors, useful as tumor suppressors (US Pat. Application Publication No. 2007/0055065).

Inhibition constants for some compounds affecting plasmin activity have been published in several studies on inhibitors of coagulation proteases. The compounds in question, however, were being investigated as antithrombotics, and therefore a low level of plasmin inhibition was preferred. For example, the thrombin inhibitor melagatran inhibits plasmin with a $K_i$ value of 0.7 µM, and the structurally related compound H317/86 has an inhibition constant of 0.22 µM (Gustafsson et al., *Thromb. Haem.*, 79, 110-118, 1998). However, because both compounds inhibit the protease thrombin much more strongly ($K_i$≤2 nM), the net effect of administration is inhibition of coagulation. The possibility of using such compounds as pro-coagulants, e.g. for reducing blood loss in cardiac surgical procedures, was not mentioned in any of these papers.

As noted above, aprotinin inhibits not only plasmin but also plasma kallikrein (PK). PK is a multifunctional, trypsin-like serine protease for which several physiological substrates are known. Thus, by proteolytic cleavage, PK is able to release the vasoactive peptide bradykinin from high molecular weight kininogen, and to activate zymogens such as coagulation factor XII, pro-urokinase, plasminogen and pro-MMP 3. It is therefore assumed that the PK/kinin system plays an important role in many pathological conditions, for example in thromboembolic situations, disseminated intravascular coagulation, septic shock, allergies, the postgastrectomy syndrome, arthritis and ARDS (adult respiratory distress syndrome) (Tada et al., *Biol. Pharm. Bull*, 24, 520-524, 2001).

Accordingly, aprotinin, via its inhibitory effect on PK, inhibits the release of the peptide hormone bradykinin, which in turn has various effects via activation of the bradykinin B2 receptor. The bradykinin-induced release of tPA, NO and prostacyclin from endothelial cells (Schmaier, *J. Clin. Invest.*, 109, 1007-1009, 2002) influences fibrinolysis, blood pressure and inflammatory events. It has been suggested that systemic inflammatory processes which may occur as a side effect in surgical operations can be reduced by inhibiting bradykinin release.

Various bisbenzamidines, such as pentamidine and related compounds, and esters of ω-amino- and ω-guanidinoalkyl-carboxylic acids, have been described as PK inhibitors with micromolar $K_i$ values (Asghar et al., *Biochim Biophys Acta*, 438, 250-264, 1976; Muramatu and Fuji, *Biochim. Biophys. Acta*, 242, 203-208, 1971; Muramatu and Fuji, *Biochim. Biophys. Acta*, 268, 221-224, 1972; Ohno et al., *Thromb. Res.*, 19, 579-588, 1980; Muramatu et al., *Hoppe-Seyler's Z. Physiol. Chem.*, 363, 203-211, 1982; Satoh et al., *Chem. Pharm. Bull.*, 33, 647-654, 1985; Teno et al., *Chem. Pharm. Bull.*, 39, 2930-2936, 1991).

The first selective competitive PK inhibitors to be reported (Okamoto et al., *Thromb. Res.*, Suppl. VIII, 131-141, 1988) were derived from arginine or phenylalanine, and inhibit PK with $K_i$ values around 1 μM. Several papers on the development of competitive PK inhibitors have been published by the Okada group, with the most active compounds, derived from trans-4-aminomethylcyclohexanecarbonyl-Phe-4-carboxymethylanilide, having inhibition constants around 0.5 μM (Okada et al., Biopolymers, 51, 41-50, 1999; Okada et al., 2000, Tsuda et al., 2001). It is characteristic of these PK inhibitors that they have a relatively high $K_i$ value.

Potent 4 amidinoaniline PK inhibitors, with $K_i$ values around 1 nM, were described in WO 00/41531, but further development of these compounds was not reported.

Garrett et al. have described transition state analogue PK inhibitors (Garrett et al., *J. Pept. Res.* 52, 60-71, 1998, Garrett et al., *Bioorg. Med. Chem. Lett.* 9, 301-306, 1999), but these compounds are prone to non-specific reaction with nucleophiles.

Aliagas-Martin et al., in U.S. Pat. No. 6,472,393, described a wide variety of 4-amidinoanilides which are potent PK inhibitors, having inhibition constants around 1 nM. Antonsson et al. likewise described a wide range of amidine and guanidine PK inhibitors in U.S. Pat. No. 5,602,253. Stürzebecher et al. have described 4-amidino- and 4-guanidino-benzylamines as PK inhibitors, some of which are Factor Xa inhibitors (US Pat. Application Publication. No. 2005/0119190), some of which have a slight inhibitory effect on plasmin (US Pat. Application Publication. No. 2006/0148901), and some of which are dual plasmin/PK inhibitors (PCT Publication No. 2008/049595).

Dyax Corp. has developed a selective plasma kallikrein inhibitor, DX-88 (ecallantide, Kalbitor™), for the treatment of acute attacks in hereditary angioedema. Ecallantide is a recombinant small protein that has been identified utilizing a phage display technology based on the first Kunitz domain of human tissue factor pathway inhibitor (TFPI). Ecallantide is also undergoing phase II clinical testing for the reduction of blood loss during on-pump cardiothoracic surgery (Lehmann, *Expert Opin. Biol. Ther.*, 8, 1187-1199, 2008).

Plasmin and plasma kallikrein, together with approximately 70 other enzymes, belong to the family of trypsin-like serine proteases which share significant sequence homology. In general, this makes it difficult to develop selective inhibitors for a particular protease based on substrate analogues. However, plasmin is missing several amino acids in a loop around the amino acid at position 99, which limits the size of the S2-pocket in most of the trypsin-like serine proteases (binding pocket terminology of Schechter and Berger, *Biochem. Biophys. Res. Comm.* 27, 157-162, 1967). This leads to a relatively open S2-pocket in the active center of plasmin, which may explain why plasmin has a very broad substrate specificity. Plasma kallikrein (PK) features a glycine at position 99, and the absence of a side chain means that plasma kallikrein also has a relatively open S2 pocket. Based on the X-ray structures of trypsin-like serine proteases in complex with substrate analogue inhibitors (Schweinitz et al., *Med. Chem.* 2, 349-361, 2006) it appears that the side chains of a P2 L-amino acid and a P3 D-amino acid (side-chain terminology of Schechter and Berger, *Biochem. Biophys. Res. Comm.* 27, 157-162, 1967) should both be directed towards the enzyme surface.

There remains a need for low-molecular-weight substances, suitable for therapeutic applications, which reversibly and competitively inhibit plasmin, and preferably plasmin and plasma kallikrein together, with high activity and specificity. The present inventors have discovered that it is possible to obtain potent inhibitors of plasmin by a suitable cyclization between the side chains of the P3- and P2-amino acids in substrate analogue inhibitors. Some of these compounds potently inhibit plasma kallikrein as well.

The compounds of the present invention, accordingly, are suitable for modulating and/or maintaining hemostasis in various situations, particularly during and after surgeries with cardiopulmonary bypass, organ transplants, and other major surgical interventions. It is expected that the compounds of the present invention, as inhibitors of plasma kallikrein, will also lower kinin release, thereby suppressing both kinin-mediated inflammatory reactions and kinin-induced release of tPA from endothelial cells. The latter effect provides an additional mechanism for downregulation of fibrinolysis.

BRIEF DESCRIPTION OF THE INVENTION

The invention provides cyclized peptide analogs of general formula I,

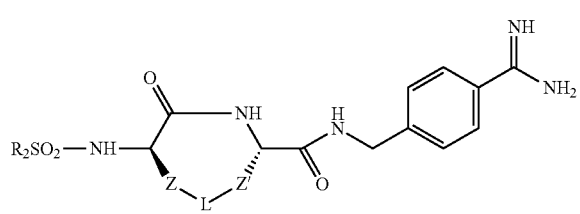

wherein the linkers Z and Z' and the bridging group L are as defined in detail below, and wherein $R^2$ is a branched, unbranched or cyclic alkyl group having 1 to 10 C atoms; a 5- or 6-membered heteroaromatic ring having 1-3 heteroatoms independently selected from N, S and O; an aryl group having 6 or 10 C atoms; or a $CH_2$ group bearing either a 5- or 6-membered heteroaromatic ring having 1-3 heteroatoms independently selected from N, S and O, or an aryl group having 6 or 10 C atoms. Heteroaryl or aryl groups may be unsubstituted or substituted with 1 to 3 residues independently selected from —CH$_2$NH$_2$, —CN, —CF$_3$, tetrazol-5-yl, F, Cl, Br, —CO$_2$H, —CO$_2$Me, —CO$_2$Et, methyl, ethyl, propyl, and isopropyl.

In preferred embodiments, the compounds of the invention have the following formula II:

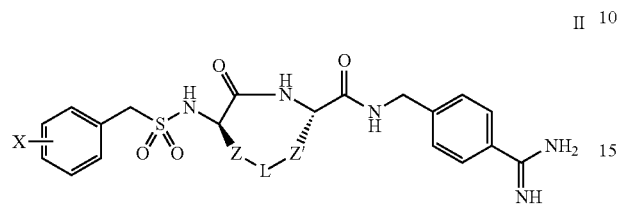

II wherein X is H, —CF$_3$, CO$_2$H, CO$_2$Me, or CO$_2$Et.

The compounds of the invention are effective and particularly selective inhibitors of human plasmin, and in certain embodiments are inhibitors of both plasmin and plasma kallikrein. The invention accordingly provides compounds of formula I, methods for the preparation of compounds of formula I, and pharmaceutical compositions comprising compounds of formula I. The invention also provides methods of inhibiting plasmin alone, or plasmin and PK, in a patient; methods for therapeutic modulation of the blood coagulation cascade and fibrinolysis; and methods for prevention and treatment of blood loss in a patient, by administration of the compounds of formula I.

The invention further provides methods for the use of these compounds in manufacturing medicaments for inhibiting plasmin alone or plasmin and PK in a patient, and medicaments for therapeutic modulation of the coagulation cascade and fibrinolysis, especially for prevention and treatment of blood loss in a patient. Subjects who may be treated with the compositions of the invention include, but are not limited to, patients experiencing hyperfibrinolytic conditions, organ transplants, and cardiac surgical procedures, especially those involving cardiopulmonary bypass.

The present invention also provides a fibrin adhesive comprising the compounds of the invention, and methods for the use of the compounds of the invention in the manufacture of a fibrin adhesive.

DETAILED DESCRIPTION OF THE INVENTION

The invention provides cyclized peptide analogs of general formula I,

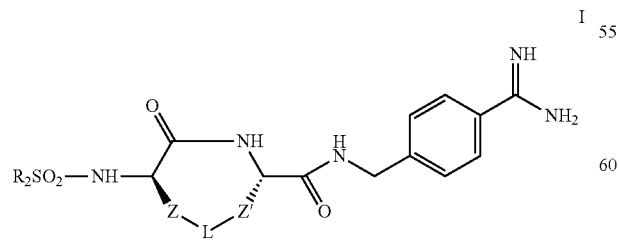

I and pharmaceutically acceptable salts thereof; wherein R$^2$ is as defined above. The linkers Z and Z' are independently selected from among the following moieties:

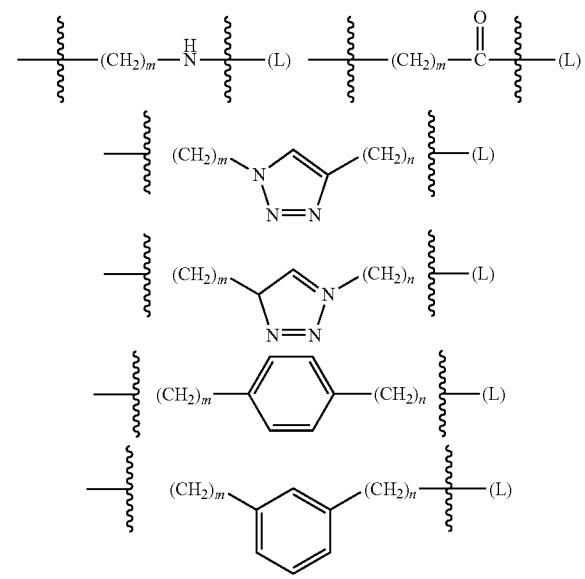

wherein the values of m and n are independently in the range 0-3.

The bridging group L is selected from among the following divalent moieties:

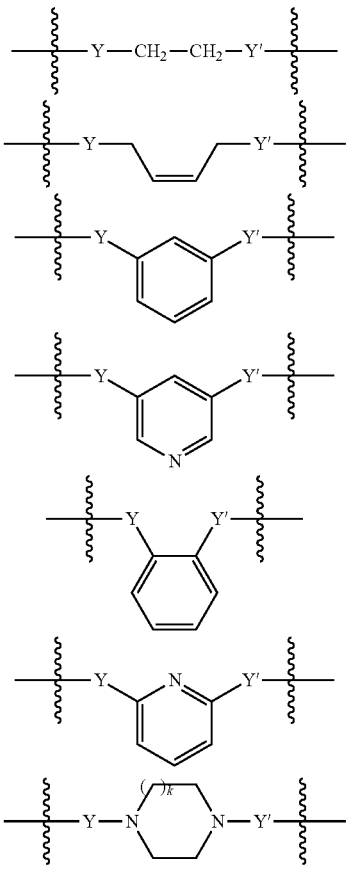

wherein k is 1 or 2, Y and Y' are independently selected from: a covalent bond, —(CH$_2$)$_p$—, —(CH$_2$)$_p$O(CH$_2$)$_q$—, —(CH$_2$)$_p$NH(CH$_2$)$_q$—, —(CH$_2$)$_p$S(CH$_2$)$_q$—, —(CH$_2$)$_p$SS (CH$_2$)$_q$—, (CH$_2$)$_p$C(=O)(CH$_2$)$_q$—, —(CH$_2$)$_{13}$NHC(=O) (CH$_2$)$_q$—, —(CH$_2$)$_p$C(=O)NH(CH$_2$)$_q$—, —(CH$_2$)$_p$OC (=O)(CH$_2$)$_q$—, —(CH$_2$)$_p$OC(=O)NH(CH$_2$)$_q$—, —(CH$_2$)$_p$NHC(=O)O(CH$_2$)$_q$—, —(CH$_2$)$_p$NHC(=O)NH(CH$_2$)$_q$—, —(CH$_2$)$_p$NHC(=NH)NH(CH$_2$)$_q$—, and —(CH$_2$)$_p$NHC(=O)(CH$_2$)$_q$S—. In the structures above, the moieties Y and Y', when not symmetrical, may be present in either orientation, and p and q independently range from 0 to 3.

Selected representative embodiments of compounds of formula I include, for example, the following structures:

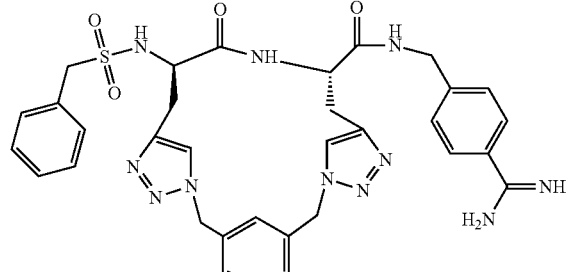

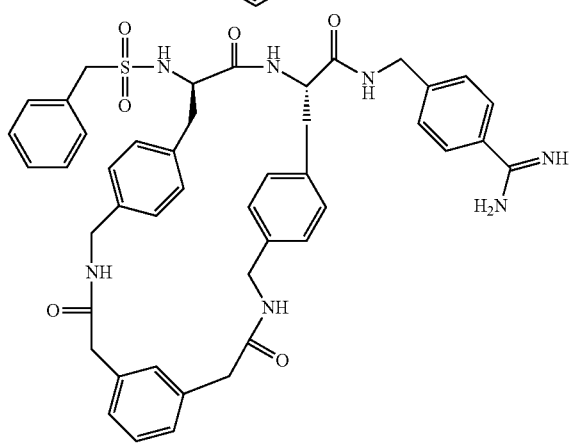

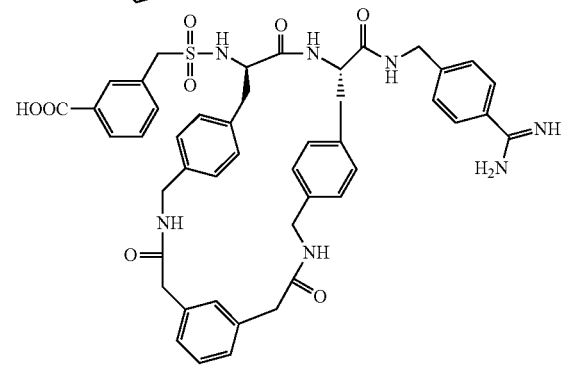

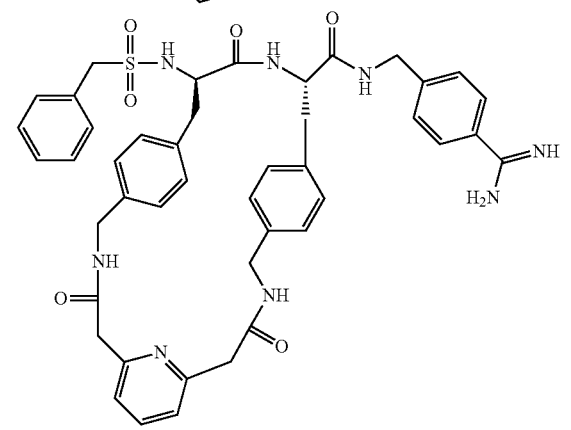

-continued

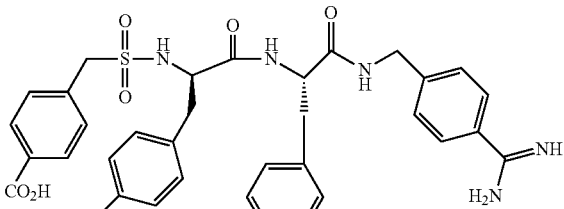

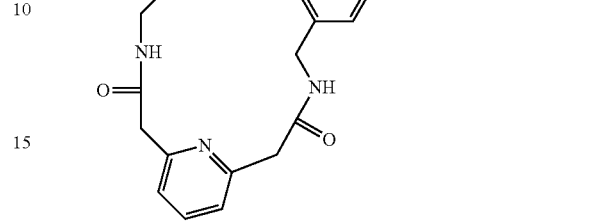

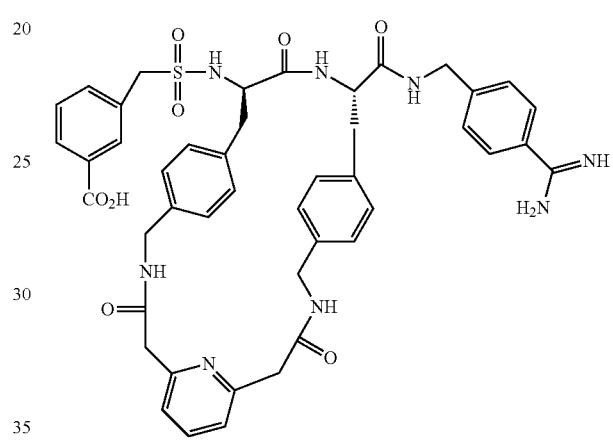

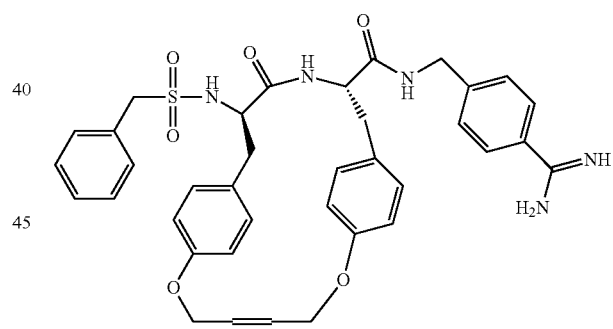

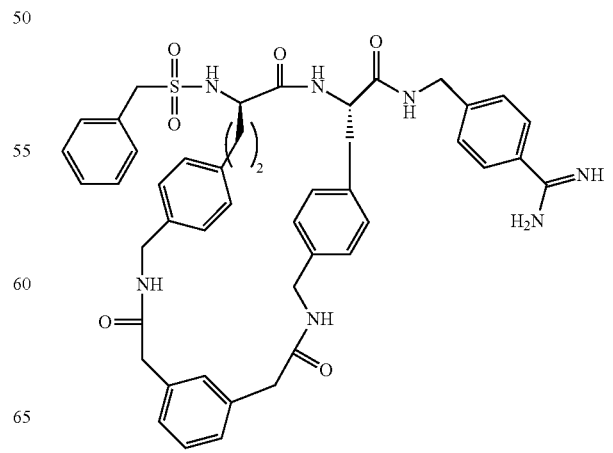

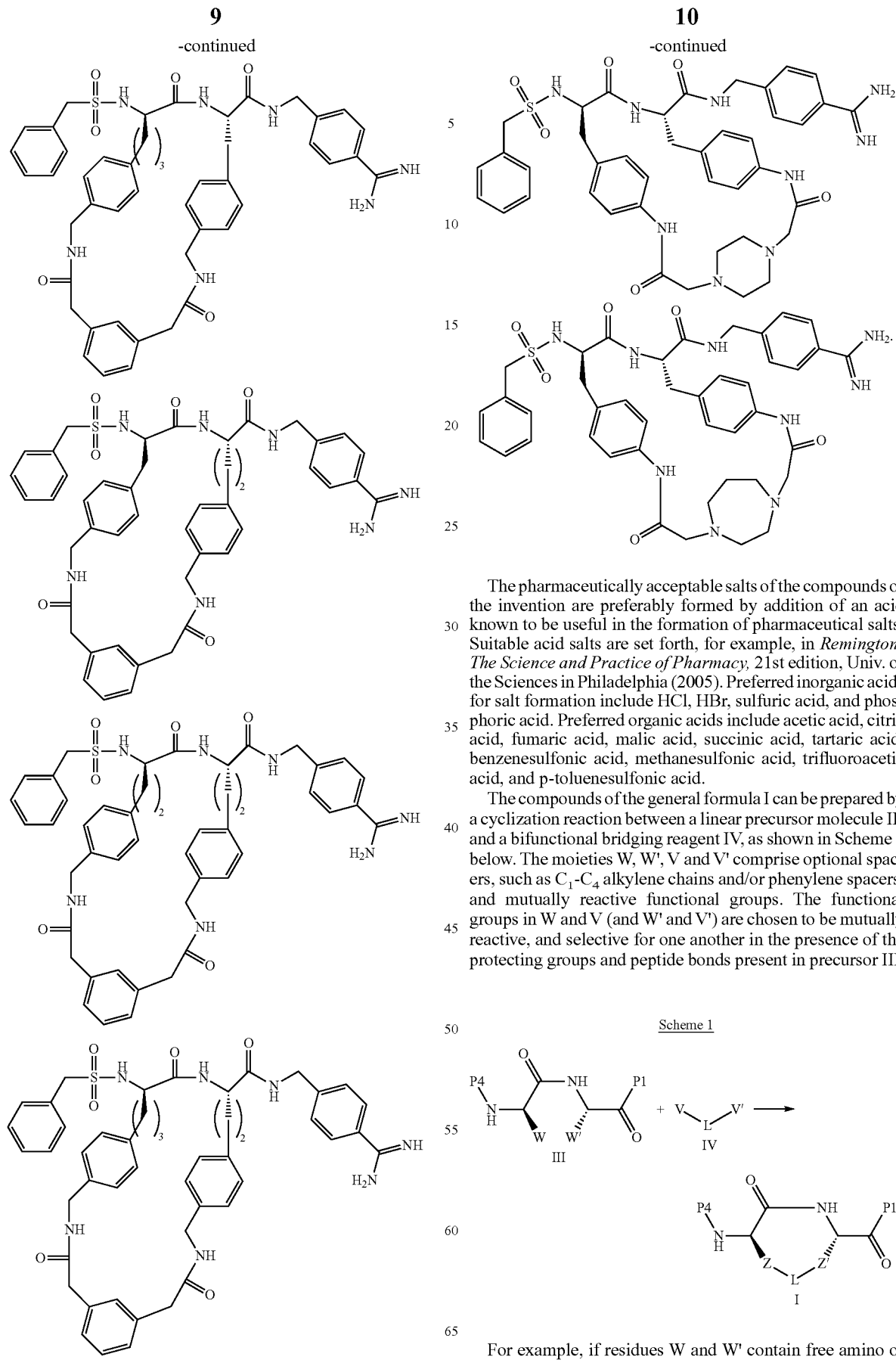

The pharmaceutically acceptable salts of the compounds of the invention are preferably formed by addition of an acid known to be useful in the formation of pharmaceutical salts. Suitable acid salts are set forth, for example, in *Remington: The Science and Practice of Pharmacy,* 21st edition, Univ. of the Sciences in Philadelphia (2005). Preferred inorganic acids for salt formation include HCl, HBr, sulfuric acid, and phosphoric acid. Preferred organic acids include acetic acid, citric acid, fumaric acid, malic acid, succinic acid, tartaric acid, benzenesulfonic acid, methanesulfonic acid, trifluoroacetic acid, and p-toluenesulfonic acid.

The compounds of the general formula I can be prepared by a cyclization reaction between a linear precursor molecule III and a bifunctional bridging reagent IV, as shown in Scheme 1 below. The moieties W, W', V and V' comprise optional spacers, such as $C_1$-$C_4$ alkylene chains and/or phenylene spacers, and mutually reactive functional groups. The functional groups in W and V (and W' and V') are chosen to be mutually reactive, and selective for one another in the presence of the protecting groups and peptide bonds present in precursor III.

Scheme 1

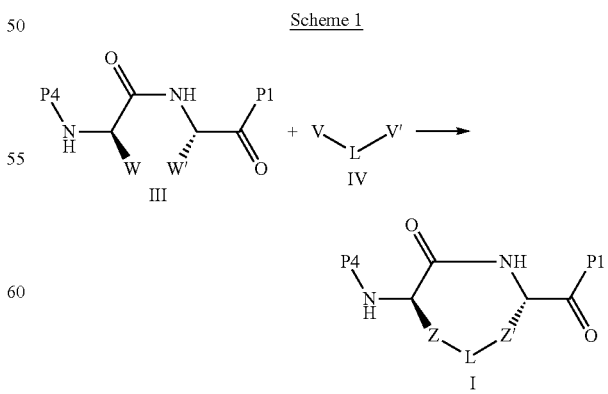

For example, if residues W and W' contain free amino or imino groups, then a cyclization can be performed using as reagent IV an aliphatic, aromatic or heteroaromatic di-carboxylic acid chloride, di-carboxylic acid active ester, or a dicarboxylic acid in the presence of a coupling reagent, such as PyBOP, HBTU, DCC, isobutylchloroformate or the like. Suitable coupling reagents and methods are well-known in the art of peptide synthesis.

If residues W and W' contain carboxylic acid groups, a cyclization can be performed using as reagent IV an aliphatic, aromatic or heteroaromatic diamine, and forming amide bonds in presence of an appropriate coupling reagent.

If residues W and W' contain alkyne groups, a copper(I) catalyzed 1,3-dipolar cycloaddition, leading to 1,4-disubstituted triazoles in the linkers Z and Z', can be carried out by employing an aliphatic, aromatic or heteroaromatic bis-azide as reagent IV. Conversely, if residues W and W' contain azide moieties, similar copper(I) catalyzed 1,3-dipolar cycloadditions can be performed using an aliphatic, aromatic or heteroaromatic dialkyne as reagent IV, again generating cyclised product I having 1,4-disubstituted triazoles in the linkers Z and Z'.

Other well-established bond-forming reactions, suitable for use in the cyclization process of Scheme 1, will be readily apparent to those of skill in the art. In general, suitable reactions will be highly selective and high in yield. In particular, reactions suitable for so-called "click chemistry" are preferred candidates for the cyclization process. (H. C. Kolb, M. G. Finn, K. B Sharpless, *Angew. Chem. Int. Ed.*, 40:2004 (2001); E. Van der Eycken and K. B. Sharpless, "Click Chemistry", *QSAR Comb. Sci.*, 26:1115 (2007)).

In alternative embodiments, rather than employ a linking reagent IV, the residues W and W' are directly cyclized. For example, if residues W and W' contain alkene groups, an alkene metathesis (e.g., using Grubbs' ruthenium catalysts) can be performed, producing the product I wherein L is —CH=CH— connecting linkers Z and Z'. The olefinic bond may be reduced by hydrogenation if an aliphatic bond is desired in the product.

By subjecting appropriate reagents III and IV to suitable reaction conditions, as set forth above, the cyclization process of Scheme 1 yields compounds I having the following arrangements of bridge L and linkers Z and Z'. It will be appreciated that as the definitions of moieties W and W' (and V and V') are interchangeable, definitions of Z and Z' are likewise interchangeable. Thus, with respect to the precursor III, both orientations of unsymmetrical substructures are disclosed by the following representative examples of the moiety Z-L-Z':

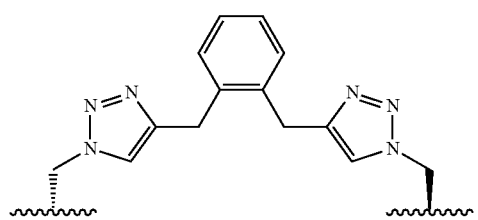

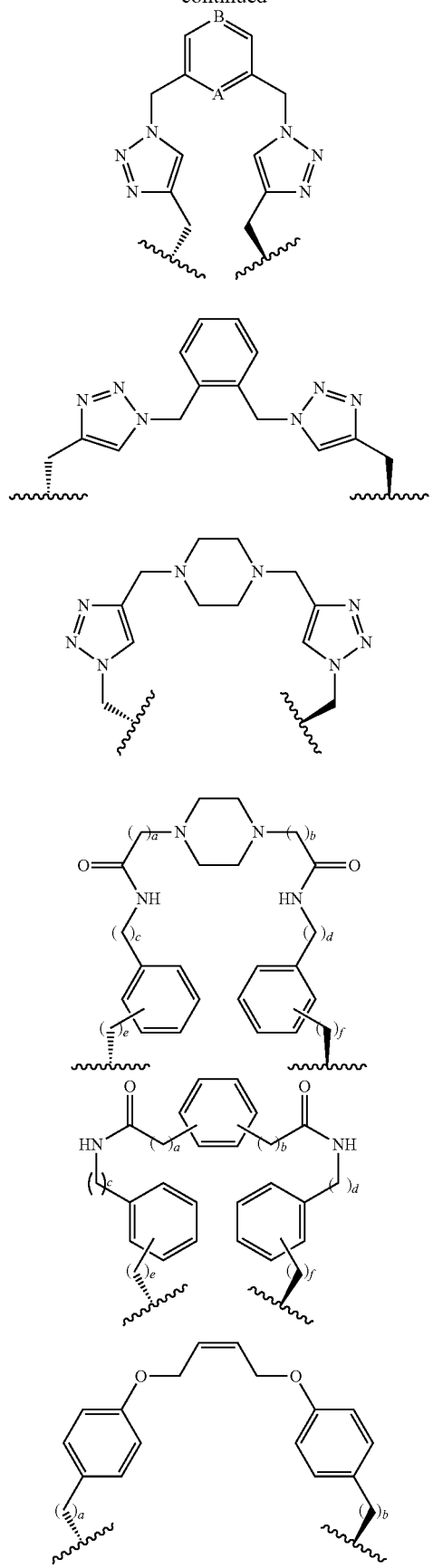

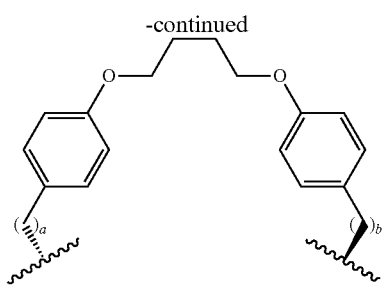

In the formulae above, A and B are independently CH or N. The values of a, b, c, d, e and f are independently 0, 1, 2 or 3.

The precursors of formula III are readily prepared by sequential coupling of amino acids to 4-amidinobenzylamine, which is N-protected at the amidino group by protecting group PG1, followed by sulfonylation. It will be understood that any suitable N-protecting group known in the art may be employed at the amidino group. Suitable N-protecting groups for the amidino group include, but are not limited to, 1,2,4-oxadiazol-5-one, 5-methyl-1,2,4-oxadiazole, N-Boc, N-Cbz, N-benzyloxy, and N-acetoxy. The 1,2,4-oxadiazol-5-one, 5-methyl-1,2,4-oxadiazole, N-benzyloxyamidino, and N-acetoxyamidino groups are preferred, because they are easily prepared from the corresponding nitrite.

The precursors III may be prepared in several ways. Preferred synthetic approaches involve the formation of amide and sulfonamide bonds between pre-synthesized components. The methods and procedures described in PCT Publication No. 2008/049595, which is incorporated herein by reference in its entirety, may be readily adapted to the synthesis of the compounds of the present invention.

As used herein, the expression "an activated carboxylic acid derived from" a given acid refers to derivatives of carboxylic acids that are reactive toward amines, including but not limited to active esters, mixed anhydrides, and acyl halides, as are well-known in the art of peptide synthesis. Suitable examples include, but are not limited to, N-hydroxybenzotriazole esters, O-acylated isoureas, pentachloro- and pentafluoro-phenyl esters, phosphonium esters, acyl chlorides, and mixed anhydrides with carbonic acid monoesters. Preferred activated carboxylic acids are N-hydroxybenzotriazole esters, and the mixed anhydrides obtained by reaction with isobutyl chloroformate.

A first representative synthesis is illustrated by the preparation of compounds of formula

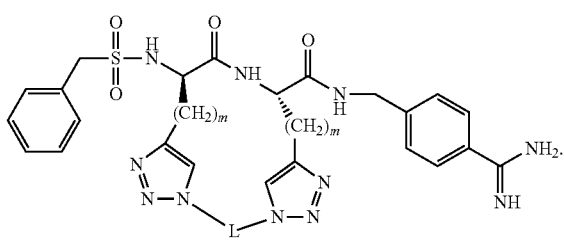

An amidino-protected 4-(aminomethyl)benzamidine, such as 4-(aminomethyl)-N-acetoxybenzamidine (i), is obtained from the commercially available 4-cyanobenzylamine (Showa Denko K.K., Japan) by the method described in the supplement to Schweinitz et al., *J. Biol. Chem.*, 279, 33613-33622 (2004). Alternative protected 4-(methylamino)-benzamidines include (ii), (iii), (iv), (v), or (vi) as described below. This material is N-acylated with an activated carboxylic acid derived from compound A

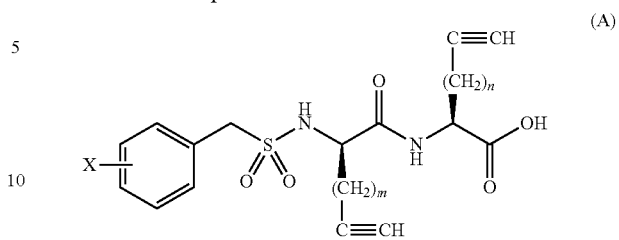

(A)

wherein X may be, for example, H, —CN, —CF$_3$, tetrazol-5-yl, F, Cl, Br, —CO$_2$Me, —CO$_2$Et, methyl, ethyl, propyl, or isopropyl; and m and n may be, for example 1, 2, 3, or 4. Following the acylation, copper- or ruthenium-catalyzed cyclization with a bis-azide N$_3$-L-N$_3$, as described above, and cleavage of the protecting group from the benzamidine are carried out, providing a compound of formula I. On a small scale, final purification of the inhibitors of formula I is preferably carried out by preparative reversed-phase HPLC. Larger preparations are purified by ion exchange or counter-current column chromatography, and/or by recrystallization of the compound, or a suitably crystalline salt thereof, as is routine in the art.

A second representative synthesis comprises the acylation of 4-(aminomethyl)-N-acetoxybenzamidine (i) (or, alternatively, (ii), (iii), (iv) or (v)) with an activated carboxylic acid derived from compound B,

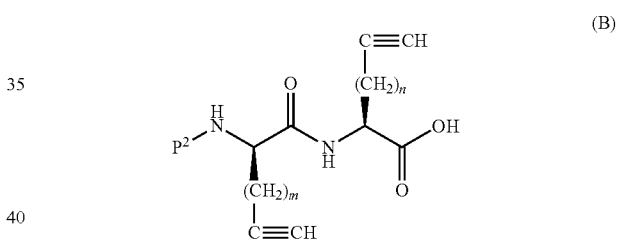

(B)

wherein P$^2$ is an amino protecting group and m and n are as described above. P$^2$ may be any amino protecting group known in the art, including but not limited to Fmoc, Alloc, Boc, benzyloxycarbonyl (Cbz), 4-nitrobenzyloxycarbonyl (4-NO$_2$—Cbz), trifluoroacetyl, trityl, and benzhydryl. Cyclization with a bis-azide may be carried on compound B (or on an ester thereof), or at any point among the subsequent transformations.

After the acylation, the amino protecting group P$^2$ is cleaved, and the resulting deprotected α-amino group is sulfonylated with a sulfonylating agent, for example as shown by formula C:

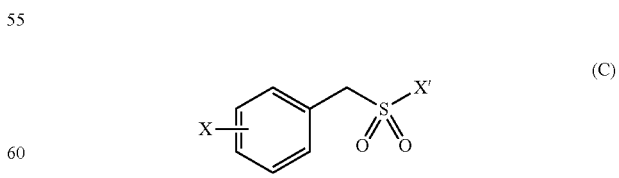

(C)

wherein X' is a leaving group, preferably Cl, and X is as defined above. After sulfonylation, the amino protecting group on the benzamidine is cleaved as described above.

A third, and preferred, synthetic approach comprises the acylation of 4-(aminomethyl)-N-acetoxybenzamidine (i) (or, alternatively, any of (ii), (iii), (iv), (v) and (vi)) with an activated carboxylic acid derived from compound D

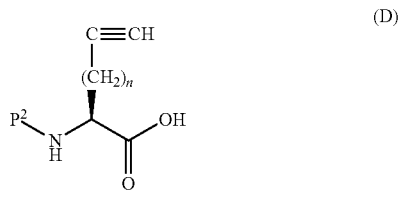

wherein P² is an amino protecting group as described above. After the acylation, the amino protecting group P² is cleaved, to generate an intermediate such as E:

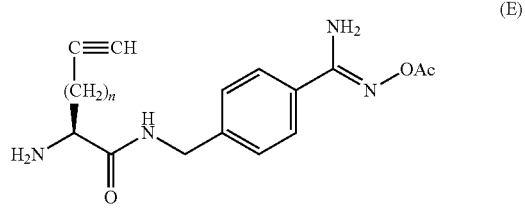

The intermediate E may then be acylated with an activated carboxylic acid derivative derived from compound F

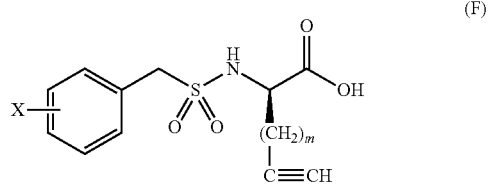

where X and m are as defined above. Cyclization with a bis-azide according to Scheme 1, followed by removal of the amidine protecting group, as described above, provides a compound of structure I.

A fourth method comprises acylation of an N-acylated amidino-protected 4-(aminomethyl)benzamidine, such as structure E

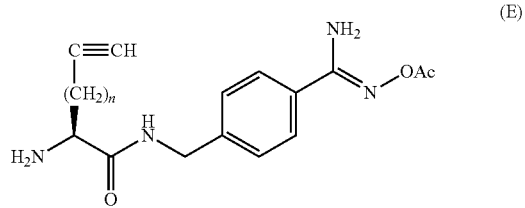

with an activated carboxylic acid derived from structure G

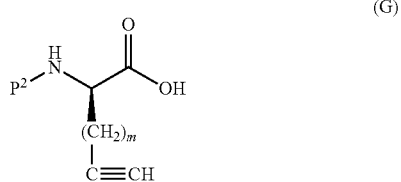

where P² and n are as defined above, to yield an intermediate such as structure H

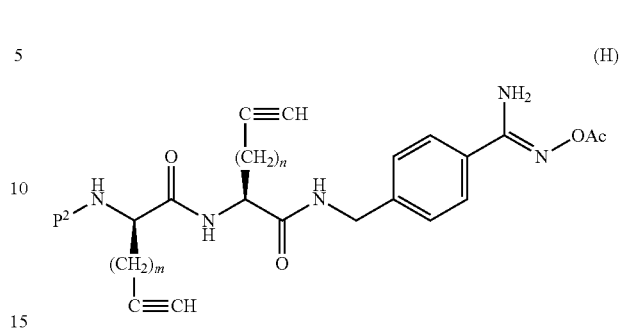

Cyclization according to Scheme 1 may be carried out at this point, or at any point among the subsequent transformations. The amino protecting group P² is then cleaved from intermediate H, and the resulting deprotected α-amino group is sulfonylated with a sulfonylating agent of formula C as described above. After sulfonylation, the protecting group on the benzamidine is cleaved as described above.

The synthesis compounds of formula

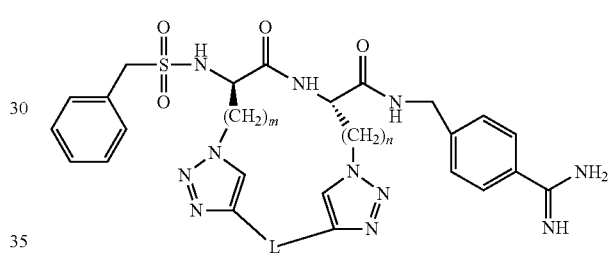

may similarly be carried out, by cyclization of a bis-alkyne of formula HC≡C-L-C≡CH with an ester, amide, or protected acid derived from a bis-azido dipeptide of structure (J):

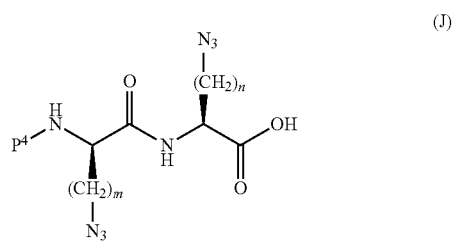

(Azido-amino acids are readily prepared; see, e.g., A. J. Link et al., *J. Am. Chem. Soc.*, 126, 10598-10602, 2004.). In structure J, P⁴ may be a protecting group P² as described above, which is subsequently removed and replaced in a sulfonylation reaction, or alternatively P⁴ may represent the sulfonyl group (R²SO₂—) desired in the final product.

In additional embodiments of the invention, any of the above methods of preparation are carried out using alternative protecting groups for the amidine functionality. Suitable protecting groups include, but are not limited to, substituted and unsubstituted N-benzyloxy, N-benzoyloxy and N-benzyloxycarbonyl groups, and the 1,2,4-oxadiazole and 1,2,4-oxadiazol-5-one heterocyclic rings, which are readily introduced by the substitution for (i) of alternative starting materials such as (ii)-(vi) shown below.

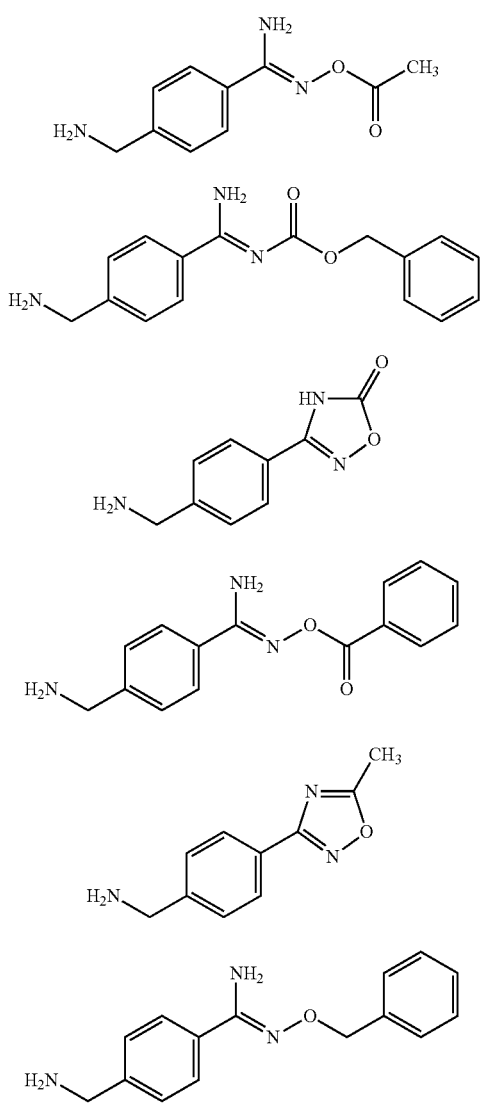

(i)
(ii)
(iii)
(iv)
(v)
(vi)

An alternative scheme, described in the examples below, employs the same reagents, but carries a 4-cyano group on P1 through the cyclization (Scheme 2). In this approach, the amidine group is generated in the final step in the synthesis:

Scheme 2

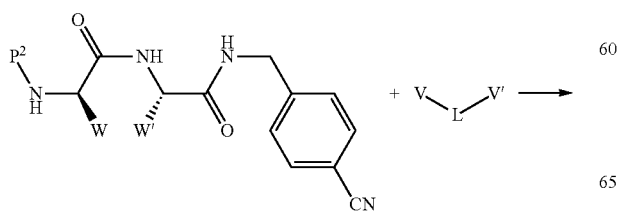

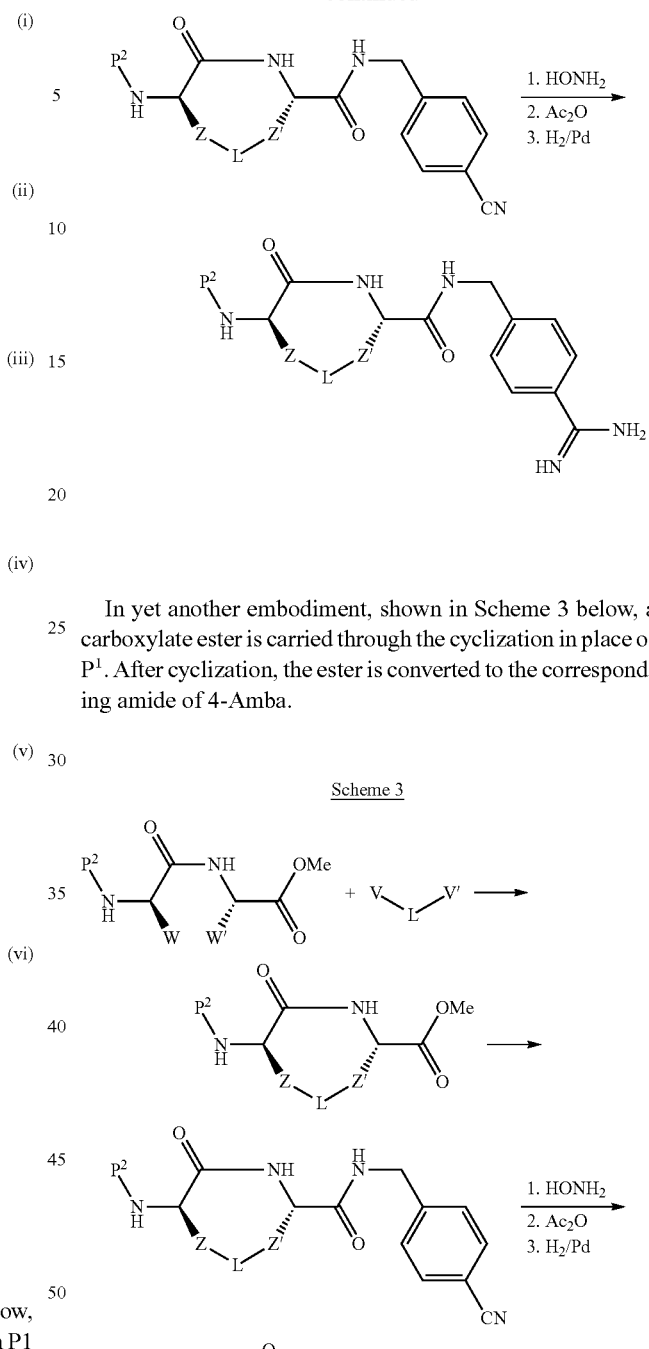

In yet another embodiment, shown in Scheme 3 below, a carboxylate ester is carried through the cyclization in place of $P^1$. After cyclization, the ester is converted to the corresponding amide of 4-Amba.

Scheme 3

Schemes 2 and 3 may be abbreviated by coupling an ester, amide, or protected acid derived from a compound of formula

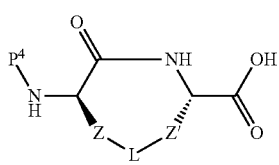

with 4-(aminomethyl)benzamdine (4-Amba)

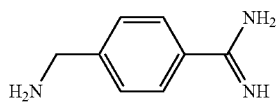

to produce a compound of formula

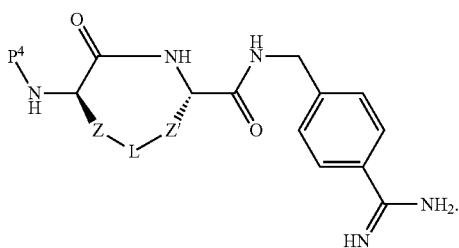

In schemes 2 and 3 above, $P^4$ may represent a conventional amino protecting group $P^2$, as defined above, which is subsequently removed and replaced in a sulfonylation reaction, or alternatively $P^4$ may represent the sulfonyl group ($R^2SO_2$—) desired in the final product. Suitable amides derived from the carboxyl group include, but are not limited to, the 4-cyanobenzyl amide; suitable esters include, but are not limited to, the methyl and trimethylsilyl esters, and suitable protected acids include, but are not limited to, ethyl, t-butyl and benzyl esters.

In another representative method, compounds of formula

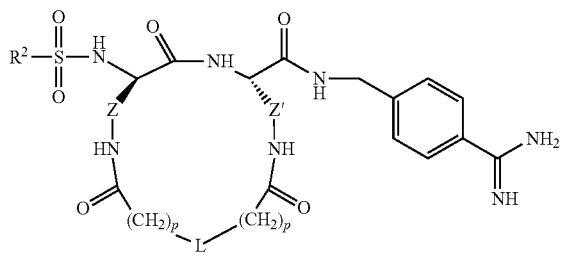

are prepared by coupling an amide, ester, or protected acid derived from a compound of formula

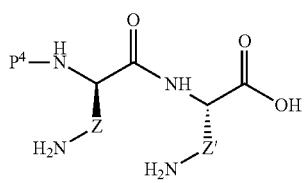

with a bis-carboxylic acid of formula HOOC—$(CH_2)_p$-L-$(CH_2)_p$—COOH to form the corresponding amide, ester, or protected acid derived from a compound of formula

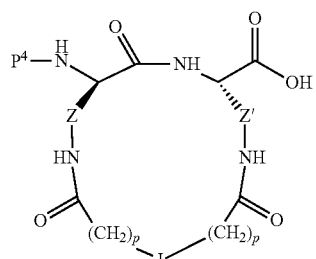

Again, the group $P^4$ may be an amino protecting group $P^2$ or the group ($R^2SO_2$—).

Additional embodiments will be apparent to those of skill in the art, wherein one or more of the steps that effect the conversion of a carboxylate to an amide, conversion of a nitrile to an amidine, and sulfonylation, may be carried out before or after the cyclization.

The compounds of the invention are useful for the therapeutic modulation of the blood coagulation cascade and fibrinolysis. As used herein, "therapeutic modulation" includes both pro- and anti-coagulant activities, and the in vivo stabilization or promotion of innate hemostatic or fibrinolytic activities. In particular, the compounds are useful for the prevention or treatment of blood loss. Patients in need of such treatment include those undergoing surgery (especially those procedures, such as cardiac surgery, which involve cardiopulmonary bypass), and those suffering from an acquired or inborn derangement of hemostasis or fibrinolysis.

The invention also provides pharmaceutical composition comprising one or more compounds of the invention, in combination with one or more pharmaceutically acceptable carriers or excipients. Such excipients include, but are not limited to, fillers, binding agents, lubricants, preservatives, water, buffers, and disintegrants. The compositions may be in the form of solids or liquids, compounded for oral administration, or solutions or suspensions suitable for parenteral administration. In particular, a buffered saline solution suitable for parenteral administration is provided, as are powdered or lyophilized compositions suitable for reconstitution into a buffered saline solution.

Also provided are fibrin adhesives comprising, in at least one component of the fibrin adhesive, one or more compounds of formula I. Methods and compositions for fibrin adhesives are well-known in the art; see Sierra, *J. Biomater. Appl.*, 7:309-352 (1993). Fibrin adhesives generally consist of a physiological two-component adhesive which comprises as a first component fibrinogen, factor XIII and aprotinin, and as a second component thrombin and calcium chloride for factor XIII activation. In such compositions, the prior art material aprotinin will be augmented or replaced by a suitable plasmin inhibitor of the present invention. Methods and materials for preparing fibrin adhesives are described in U.S. Pat. No. 7,572,769, which is incorporated by reference in its entirety. Compositions without fibrinogen may also be prepared, as described in U.S. Pat. No. 6,410,260, which is incorporated herein by reference in its entirety.

The invention also provides methods for preventing blood loss in a patient, which comprise administering to a patient in need thereof an effective amount of at least one compound of formula I. Such patients include, but are not limited to, individuals with hyperfibrinolytic conditions, or undergoing organ transplants or cardiac surgical procedures, in particular those procedures involving cardiopulmonary bypass. Preferably the compound or compounds are administered in the form of a pharmaceutical composition as described above. Those skilled in the art will appreciate that suitable doses will vary with the particular compound, the route of administration, the condition to be treated, and the hemostatic status of the patient. In general, daily doses in the range of 1 mg to 500 mg will be effective. Effective dosing levels can be determined by routine dose-ranging studies, which are well within the ability of those skilled in the art. Dosing may be continuous (e.g., via an intravenous line), or unit doses can be administered one or more times daily, as needed to maintain an effective concentration in vivo. Preferably, dosing is adjusted so as to maintain a mean blood level ranging from 0.01 to 10 μg/ml during the period for which prevention of blood loss is desired.

The invention further provides methods for inhibiting human plasmin alone, or plasmin and PK, in a patient in need thereof, comprising administering to said patient an effective amount of one or more compounds of formula I. Effective doses are determined as described above.

The invention also provides for the use of a compound of formula I in the manufacture of medicaments for the prevention of blood loss, for the inhibition of plasmin alone, or for the inhibition of plasmin and PK, and in the manufacture of a fibrin adhesive.

The following examples are presented by way of example, and are intended to illustrate and explain the invention in detail. The scope of the invention is not limited to the examples presented.

EXAMPLES

Analytical HPLC

| Variable | Parameters |
|---|---|
| Device | Shimadzu LC-10A system with photodiode array detector |
| Column | Nucleodur ™ 100-5 C18 ec, 250 × 4.6 mm, Macherey-Nagel, Düren, Germany |
| Mobile phase | A: TFA, 0.1%(v/v) in water; B: TFA, 0.1%(v/v) in acetonitrile |
| Method | Linear gradient, 1% increase in solvent B per min |
| Flow rate | 1.0 mL/min |
| Detection | UV 220 nm |
| Column temperature | 30° C. |

Preparative HPLC

| Variable | Parameters |
|---|---|
| Device | Varian PrepStar ™ 218 |
| Column | A: Nucleodur ™ C8, 5 μm, 100 Å, 32 × 250 mm, Macherey-Nagel, Düren, Germany<br>B: Prontosil ™ 120-5-C18-SH, 32 × 250 mm, Bischoff, Leonberg, Germany<br>(Column A was used routinely, column B was used where noted.) |
| Mobile phase | A: TFA, 0.1%(v/v) in H$_2$O; B: TFA, 0.1%(v/v) in acetonitrile |
| Method | Linear gradient |
| Flow rate | 20.0 mL/min |
| Detection | UV 220 nm |
| Column temperature | (ambient) |

Thin Layer Chromatography

Thin layer chromatography (TLC) of final inhibitors was performed on silica gel plates (Adamant™ UV254, Machery-Nagel, Düken, Germany) using n-butanol/acetic acid/water 4/1/1 (v/v/v). Spots were detected by UV-absorbance, followed by treatment with ninhydrin spray, or by incubation of the TLC plates in a chlorine atmosphere and visualization with o-toluidine.

Mass Spectroscopy

Mass spectra were recorded on a QTrap™ 2000 ESI spectrometer (Applied Biosystems), or an Autospec™ spectrometer (Micromass).

NMR Spectroscopy $^1$H and $^{13}$C spectra were recorded at 400 and 100 MHz, respectively, on an ECX-400 spectrometer (Jeol Inc., USA), and are referenced to internal solvent signals.

ABBREVIATIONS 4-(aminomethyl)benzamidine

Ac acetyl

AMe aminomethyl

Boc tert.-butyloxycarbonyl

BSA bovine serum albumin

Bzl benzyl

Bzls benzylsulfonyl

Cbz benzyloxycarbonyl

DCM dichloromethane

DIPEA diisopropylethylamine

DMF N,N-dimethylformamide

DMSO dimethyl sulfoxide

HBTU 2-(1H-benzotriazol-1-yl)-1,1,3,3-tetramethyluronium hexafluorophosphate

HPLC high performance liquid chromatography

MTBE t-butylmethylether

MS mass spectroscopy

NMM N-methylmorpholine

Phe(4-NH$_2$) 4-aminophenylalanine

Phe(4-AMe) 4-aminomethylphenylalanine

Phe(4-CN) 4-cyanophenylalanine

Phe(4-NO$_2$) 4-nitrophenylalanine

Ppg propargylglycine

PyBop benzotriazol-1-yl-oxytripyrrolidinophosphonium hexafluorophosphate

TFA trifluoroacetic acid

THF tetrahydrofuran

TLC thin layer chromatography

TMS-Cl trimethylsilyl chloride

Commercial chemicals, solvents, reagents and amino acid derivatives were purchased from the companies Aldrich, Fluka, Acros, Bachem, Iris Biotech, Orpegen Pharma, Novabiochem and Peptech.

Example 1

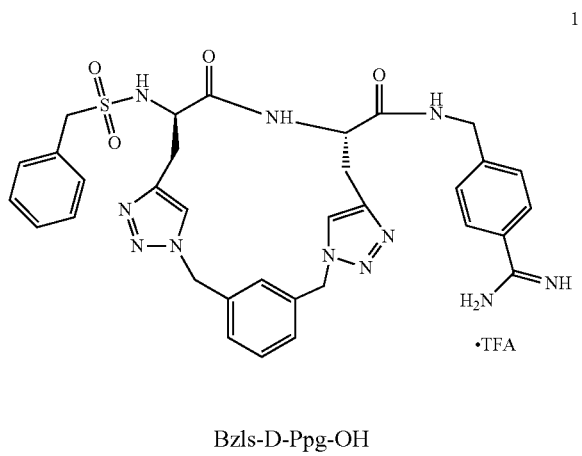

Bzls-D-Ppg-OH

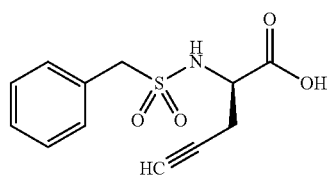

500 mg (3.34 mmol) H-D-Ppg-OH.HCl was suspended in 10 ml dry DCM and treated with 912 μl (7.35 mmol) TMS-Cl and 1.861 ml (10.69 mmol) DIPEA. The mixture was refluxed for one hour. At 0° C., 705 mg (3.70 mmol) benzylsulfonyl chloride was added in several portions over 35 min. The pH was maintained at 8-9 by addition of additional DIPEA (700 μl, 4.02 mmol). The mixture was stirred on the ice bath for 30 min and at room temperature overnight.

The solvent was removed in vacuo, and the brown residue was dissolved in water adjusted to pH 8-9 (with 1 N NaOH). The solution was extracted 2× with EtOAc, the water phase was adjusted to pH 1 with a 5% KHSO$_4$ solution and extracted 3× with EtOAc. The combined organic phase was washed 2× with 5% KHSO$_4$ and 2× with brine. The organic phase was dried with Na$_2$SO$_4$, filtered and the solvent removed in vacuo. Yield: 481 mg (brown oil, HPLC: 26.7 min, start at 10% B; MS: calc.: 267.06 found: 285 (M+NH$_4$)$^+$, 290 (M+Na)$^+$).

H-Ppg-OMe.HCl

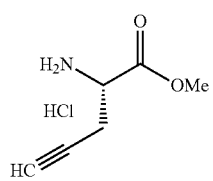

498 mg (3.33 mmol) H-Ppg-OH was suspended in 2 ml methanol and treated dropwise with 267 μl thionyl chloride at −15° C. The mixture was stirred 1 h at −15° C., and treated with additional 27 μl thionyl chloride at room temperature. The mixture was stirred overnight at room temperature and the product was precipitated by addition of diethyl ether. The product was obtained by filtration and dried in vacuo. Yield: 490.3 mg (brown solid, MS: calc.: 127.06 found: 128 (M+H)$^+$).

Bzls-D-Ppg-Ppg-OMe

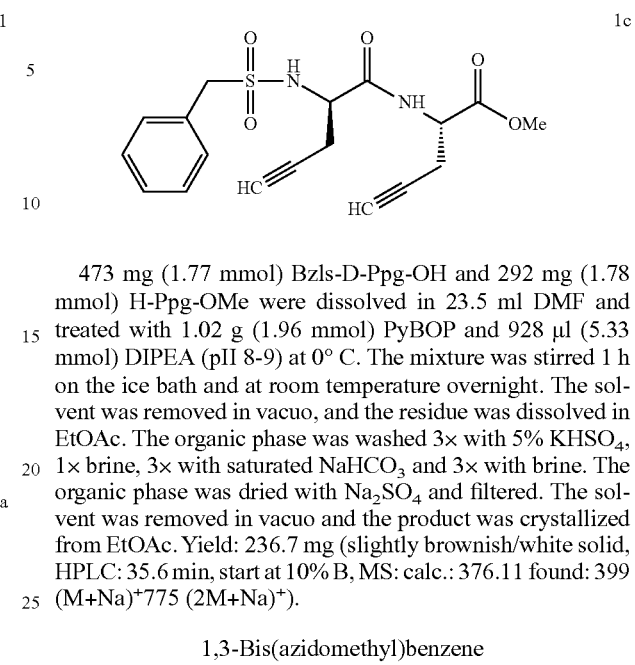

473 mg (1.77 mmol) Bzls-D-Ppg-OH and 292 mg (1.78 mmol) H-Ppg-OMe were dissolved in 23.5 ml DMF and treated with 1.02 g (1.96 mmol) PyBOP and 928 μl (5.33 mmol) DIPEA (pH 8-9) at 0° C. The mixture was stirred 1 h on the ice bath and at room temperature overnight. The solvent was removed in vacuo, and the residue was dissolved in EtOAc. The organic phase was washed 3× with 5% KHSO$_4$, 1× brine, 3× with saturated NaHCO$_3$ and 3× with brine. The organic phase was dried with Na$_2$SO$_4$ and filtered. The solvent was removed in vacuo and the product was crystallized from EtOAc. Yield: 236.7 mg (slightly brownish/white solid, HPLC: 35.6 min, start at 10% B, MS: calc.: 376.11 found: 399 (M+Na)$^+$ 775 (2M+Na)$^+$).

1,3-Bis(azidomethyl)benzene

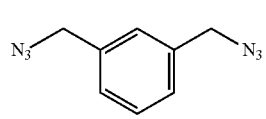

1.32 g (5.0 mmol) α,α-dibromo-m-xylene were dissolved in 30 ml DMSO and treated with 810 mg (12.5 mmol) sodium azide. The mixture was stirred 2 h at room temperature. The yellow solution was treated with ice water and extracted 3× with EtOAc. The combined organic phases were washed 2× with water and 1× with brine, dried with Na$_2$SO$_4$, filtered and the solvent evaporated. Yield: 880 mg yellow oil (HPLC: 20.8 min, start at 40% B).

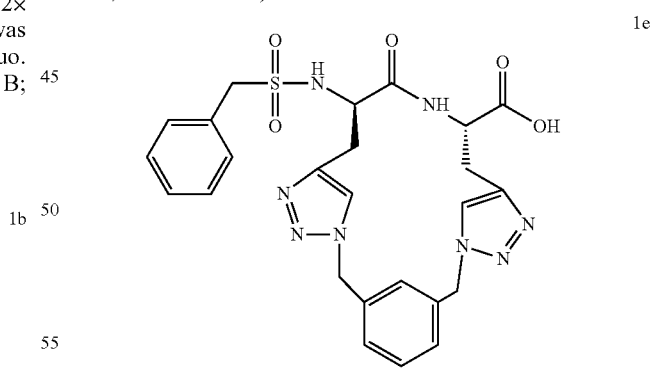

150 mg (0.399 mmol) Bzls-D-Ppg-Ppg-OMe, 63 mg (0.399 mmol) 1,3-bis(azidomethyl)benzene and 19 mg (0.159 mmol) CuBr were dissolved in 50 ml DMF, 1 ml water and 416 μl (2.391 mmol) DIPEA. The reaction was performed at 120° C. in a microwave reactor (Discover™, CEM) for 5 min (150 W, temperature priority). (See P. Cintas et al., *Coll. Czech. Chem. Commun.*, 72, 1014-1024, 2007.) The solvent was removed in vacuo and the methyl ester was obtained as a green oil. (HPLC: 13.3 min, start at 30% B, MS: calc.: 564.19 found: 565.12 (M+H)$^+$). This procedure was repeated twice.

The combined residues of these three reactions were dissolved in 30 ml DMF and treated with 3.6 ml 1 N NaOH solution. The mixture was stirred for 1 h at room temperature. The solvent was removed in vacuo, the residue was suspended in a mixture of EtOAc and 5% KHSO₄ solution. The water phase was extracted twice with EtOAc. The combined organic phases were washed 1× with 5% KHSO₄ solution, 3× with brine, dried with Na₂SO₄, filtered, and the solvent was removed in vacuo. Yield: 208 mg slightly yellow, amorphous solid (HPLC: 10.8 min, start at 30% B).

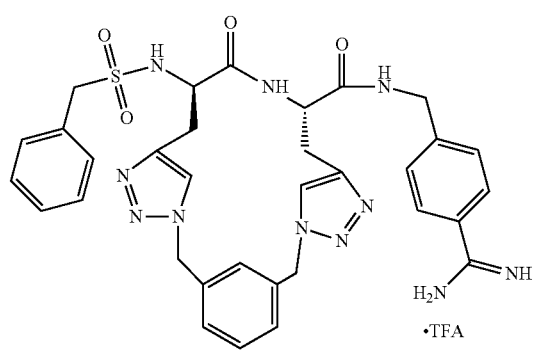

108 mg of compound 1e (0.196 mmol) and 21.6 µl NMM (0.196 mmol) were dissolved at −20° C. and treated with 25.5 µl isobutyl chloroformate (0.196 mmol). The mixture was stirred for 10 min at −15° C. and treated with 65.4 mg (0.294 mmol) 4-amidinobenzylamine.2HCl and 21.6 µl NMM (0.196 mmol). The suspension was stirred at −20° C. for an additional hour and at room temperature overnight. The solvent was removed in vacuo. The slightly yellow residue was dissolved in 35% solvent B and purified by preparative HPLC (start of the gradient at 20% B). The product containing fractions were combined and the solvent was partially removed in vacuo, followed by lyophilisation of the product. Yield: 78 mg white lyophilized solid (HPLC: 24.7 min, start at 10% B, MS: calc.: 681.26 found: 341.58 (2M+H)⁺ 682.08 (M+H)⁺, TLC: $R_f$=0.43).

Example 2

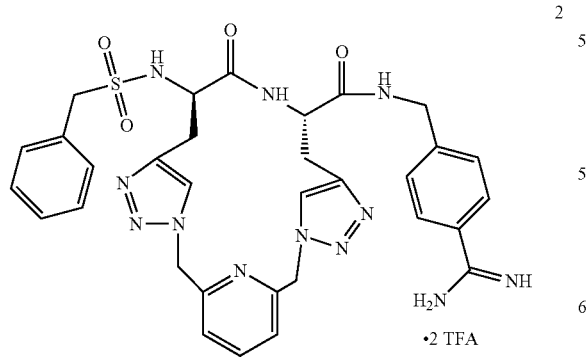

2,6-Bis(bromomethyl)pyridine (1.0 g, 3.77 mmol) was dissolved in 30 ml DMSO and treated with 613 mg (9.44 mmol) sodium azide. The mixture was stirred at room temperature for two hours. The slightly yellow solution was treated with ice water and extracted 3× with ethyl acetate. The combined organic phases were washed twice with water and 1× with brine, dried with Na₂SO₄, and filtered, and the solvent was removed in vacuo to provide 528 mg 2,6-bis(azidomethyl)pyridine (2a) as a yellow oil.

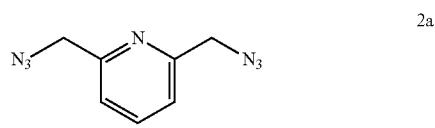 [SMILES: [N-]=[N+]=NCc1cccc(CN=[N+]=[N-])n1]

(HPLC: 19.7 min, start at 20% B, MS: calc.: 189.08 found: 190.0 (M+H)⁺.

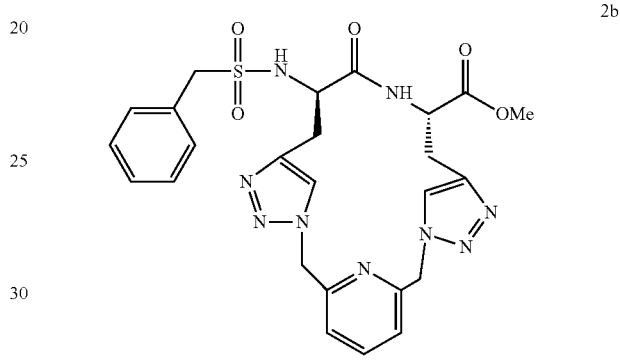

Bzls-D-Ppg-Ppg-OMe (208 mg, 0.5526 mmol), 2,6-bis(azidomethyl)pyridine (104.5 mg, 0.553 mmol), and CuBr (31.7 mg, 0.2210 mmol) were dissolved in 50 ml DMF, 1 ml water and 577 µl (3.316 mmol) DIPEA. The reaction was performed in the microwave reactor at 120° C. (5 min, 150 W, temperature priority). The solvent was removed in vacuo, and the residue was treated with a mixture of a saturated NaHCO₃ solution and ethyl acetate. The water phase was extracted twice with ethyl acetate. The combined organic phases were washed 1× with saturated NaHCO₃ and 3× with brine. Yield: 60.9 mg 2b as a white, amorphous solid (HPLC: 18.5 min, start at 20% B, MS: calc.: 565.2. found: 566.5 (M+H)⁺.

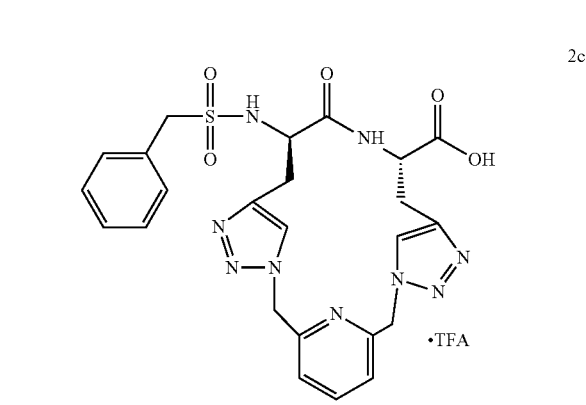 [SMILES: O=C(O)[C@@H]1Cc2cn(nn2)Cc2cccc(n2)Cn2cc(nn2)C[C@@H](NS(=O)(=O)Cc2ccccc2)C(=O)N1]

Intermediate 2b (60.9 mg, 0.1079 mmol) was dissolved in 20 ml ethanol/water and treated with 1 ml 1 N NaOH. The mixture was stirred at room temperature for two hours. The mixture was neutralized by addition of TFA and the solvent was removed in vacuo. The dark brown residue was dissolved in 30% solvent B and purified by preparative HPLC(C18 column, start of the gradient at 15% B). The product containing fractions were combined, the solvent was partially removed and the product was lyophilized. Yield: 33.4 mg 2c as a slightly yellow solid (HPLC: 13.6 min, start at 20% B, MS: calc.: 551.2. found: 552.4 (M+H)⁺).

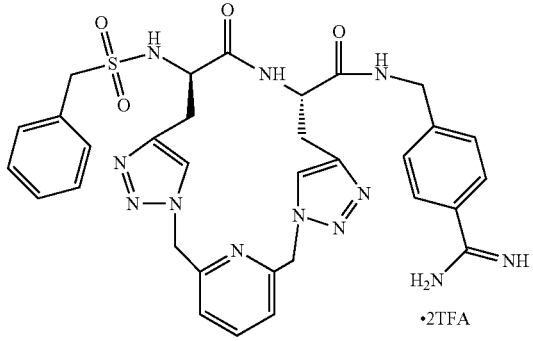

Intermediate 2c (30 mg, 0.04507 mmol) was dissolved in 5 ml DMF and treated with 5 μl NMM (0.04507 mmol). At −20° C. 5.9 μl isobutyl chloroformate (0.045 mmol) were added. After 10 min at −15° C. 15.6 mg (0.0676 mmol) 4-amidinobenzylamine.2HCl and 5 μl NMM (0.04507 mmol) were added. The mixture was stirred at −20° C. for one hour and at room temperature overnight. The solvent was removed in vacuo, and the remaining light yellow solid was dissolved in 30% solvent B and purified by preparative HPLC (column B, start of gradient at 15% B). The product containing fractions were combined, the solvent partially removed, and the product lyophilized Yield: 9.8 mg 2 as a white lyophilized powder (HPLC: 10.7 min, start at 20% B, MS: calc.: 682.76 found: 683.46 (M+H)⁺, TLC: R$_f$=0.25).

Example 3

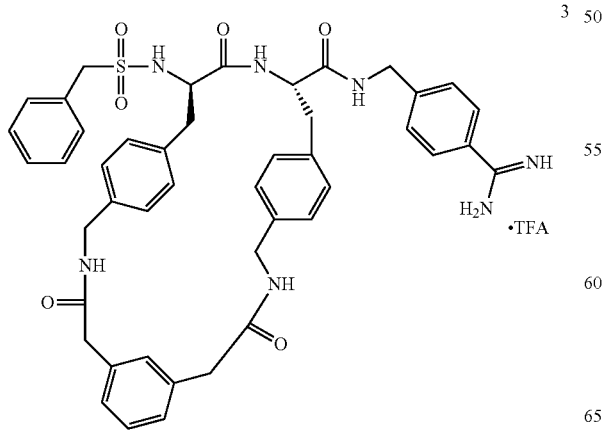

Boc-D-Phe(4-CN)—OH

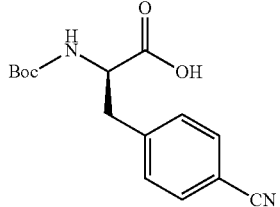

H-D-Phe(4-CN)—OH (3.0 g, 13.2 mmol) was dissolved in 14 ml t-butanol, and 20 ml water and 1.63 g (41 mmol) NaOH were added. The mixture was treated with 4.35 g (19.8 mmol) Boc₂O over a period of one hour. The mixture was stirred at room temperature overnight, and the solvent was removed in vacuo. The residue was dissolved in a mixture of 5% KHSO₄ solution and ethyl acetate, and the water phase was extracted twice with ethyl acetate. The combined organic phases were washed 3× with brine, dried with Na₂SO₄, filtered, and the solvent removed in vacuo. Yield: 3.7 g 3a as a white solid (HPLC: 35.6 min, start at 10% B).

Boc-Phe(4-CN)—OH

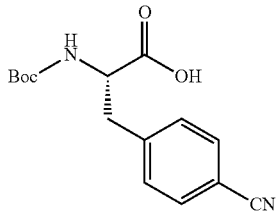

The compound 3b was prepared by the method used to prepare intermediate 3a. Yield: 2.8 g 3b as a white solid (HPLC: 35.6 min, start at 10% B).

Boc-D-Phe(4-AMe)—OH.CH₃COOH

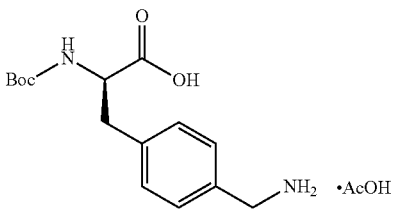

2.3 g (7.9 mmol) Boc-D-Phe(4-CN)—OH was dissolved in 450 ml AcOH (90%), and 250 mg Pd/C (10% Pd) was added. The mixture was hydrogenated with hydrogen at 40° C. overnight. The catalyst was removed by filtration and the solvent was evaporated. The residue was dissolved in a small amount of methanol and precipitated with diethyl ether. Yield: 1.7 g 3c as a white solid (HPLC: 16.8 min, start at 10% B).

Boc-Phe(4-AMe)-OH.CH₃COOH

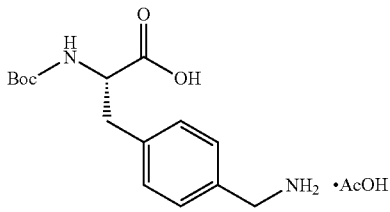
3d

The intermediate 3b (2.8 g) was converted to 3d by the method described for preparation of intermediate 3c. Yield: 2.5 g white solid (HPLC: 16.8 min, start at 10% B).

Boc-D-Phe(4-Tfa-AMe)-OH

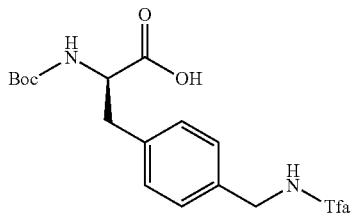
3e

Boc-D-Phe(4-AMe)—OH.CH₃COOH (1.7 g, 4.80 mmol) was suspended in 10 ml methanol and treated with 737 µl (6.195 mmol) ethyl trifluoroacetate and 1.92 ml (11.05 mmol) DIPEA. The mixture was stirred for one hour. The solvent was removed in vacuo and the residue was dissolved with a mixture of 5% KHSO₄ solution and ethyl acetate. The organic phase was washed twice with a 5% KHSO₄ solution and 3× with brine. The organic phase was dried with Na₂SO₄, filtered, and the solvent was removed in vacuo. Yield: 2.2 g 3e as a yellow amorphous solid (HPLC: 38.8 min, start at 10% B).

Boc-Phe(4-Tfa-AMe)-OH

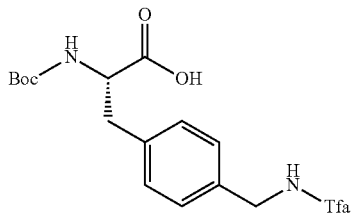
3f

Intermediate 3d (2.5 g) was converted to compound 3f by the procedure described for preparation of intermediate 3e. Yield: 3.0 g yellow amorphous solid (HPLC: 38.8 min, start at 10% B).

Boc-Phe(4-Tfa-AMe)-4-cyanobenzylamide

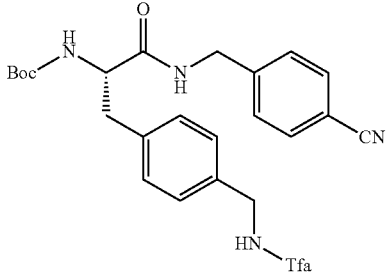
3g

Boc-Phe(4-Tfa-AMe)-OH (3f), (3.0 g, 7.81 mmol) was dissolved in 35 ml THF at −15° C. and treated with 1.02 ml (7.81 mmol) isobutyl chloroformate and 859 µl (7.81 mmol) NMM. The mixture was stirred for 10 min at −15° C., followed by treatment with 1.38 g (8.20 mmol) 4-cyanobenzylamine.HCl and 902 µl (8.20 mmol) NMM. The mixture was stirred at −15° C. for 1 h and at room temperature for 6 h. The solvent was removed in vacuo and the residue was dissolved in a mixture of 5% KHSO₄ solution and ethyl acetate, and washed 3× with 5% KHSO₄ solution, 1× with brine, 3× with saturated NaHCO₃ solution and 3× with brine. The organic phase was dried with Na₂SO₄, filtered and the solvent was removed in vacuo. Yield: 3.7 g 3g as a white amorphous solid (HPLC: 46.7 min, start at 10% B).

H-Phe(4-Tfa-AMe)-4-cyanobenzylamide.HCl

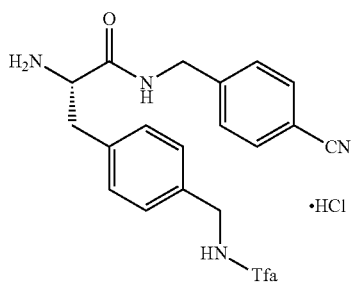
3h

Boc-Phe(4-Tfa-AMe)-4-cyanobenzylamide (3g), (3.7 g, 7.3 mmol) was treated with 42 ml 1 N HCl in acetic acid. The product was precipitated by addition of diethyl ether after 1 h. The product was obtained by filtration, washed with diethyl ether and dried in vacuo. Yield: 3.0 g 3h as a white solid (HPLC: 24.9 min, start at 10% B).

Boc-D-Phe(4-Tfa-AMe)-Phe(4-Tfa-AMe)-4-cyanobenzylamide

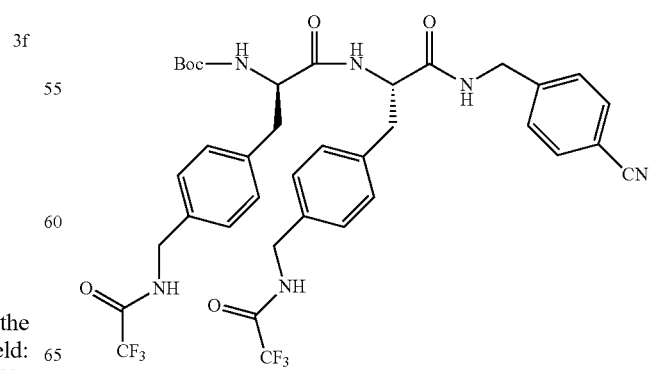
3i

Boc-D-Phe(4-Tfa-AMe)-OH (3e), (2.2 g, 5.6 mmol) and H-Phe(4-Tfa-AMe)-4-cyanobenzylamide.HCl (3h), (2.5 g, 5.6 mmol) were dissolved in 50 ml DMF. The mixture was treated at 0° C. with 2.93 g (5.6 mmol) PyBOP and 2.94 ml (16.9 mmol) DIPEA and was stirred for 2 h at 0° C. and at room temperature overnight. The DMF was removed in vacuo, the residue was treated with ethyl acetate, and the organic phase was washed 3× with 5% KHSO$_4$ solution, 1× with brine, 3× with saturated NaHCO$_3$ solution and 3× with brine. The organic phase was dried with Na$_2$SO$_4$, filtered and the solvent removed in vacuo. Yield: 5.6 g 3i as a light yellow solid (HPLC: 52.2 min, start at 10% B).

H-D-Phe(4-Tfa-AMe)-Phe(4-Tfa-AMe)-4-cyanobenzylamide.HCl

3j

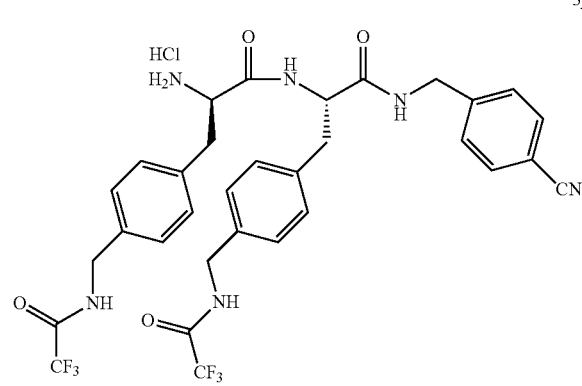

Boc-D-Phe(4-Tfa-AMe)-Phe(4-Tfa-AMe)-4-cyanobenzylamide (3i), (5.5 g, 5.63 mmol) was dissolved in 30 ml acetic acid and treated with 12 ml 1 N HCl in acetic acid. The mixture was shaken intermittently, and after 1.5 h the solvent was partially removed and the product was precipitated by addition of diethyl ether and dried in vacuo. Yield: 4.46 g 3j as a white solid (HPLC: 35.2 min, start at 10% B).

Bzls-D-Phe(4-Tfa-AMe)-Phe(4-Tfa-AMe)-4-cyanobenzylamide

3k

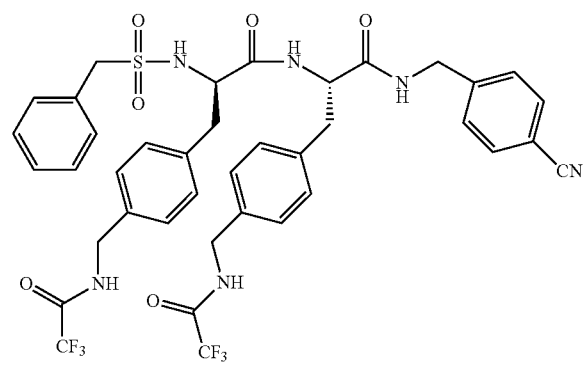

H-D-Phe(4-Tfa-AMe)-Phe(4-Tfa-AMe)-4-cyanobenzylamide.HCl (4.46 g, 6.25 mmol) was dissolved in 50 ml THF at 0° C. and treated with 1.33 g (6.9 mmol) benzylsulfonyl chloride and 1.375 ml (12.5 mmol) NMM. The mixture was stirred for two hours on the ice bath and at room temperature overnight. The mixture still contained some starting material (HPLC), therefore, additional 2.62 g (13.7 mmol) benzylsulfonyl chloride were added at 0° C. (pH adjusted to 8-9 by NMM), and the mixture was stirred for 2.5 h at 0° C., followed by evaporation of the solvent in vacuo. The residue was treated with a mixture of ethyl acetate and 5% KHSO$_4$ solution and washed 3× with 5% KHSO$_4$ solution, 1× brine, 3× with saturated NaHCO$_3$ solution and 3× with brine. Product which had precipitated between the phases was removed by filtration. Yield: 1.7 g 3k as a light gray solid, which was used as is for further reactions. (HPLC: 51.5 min, start at 10% B, MS: calc.: 830.23 found: 853.14 (M+Na)$^+$.) The remaining organic phase was dried with Na$_2$SO$_4$, filtered and the solvent was removed in vacuo to leave an additional 2.9 g 3k as a slightly yellow solid having some impurities (HPLC: 51.5 min, start at 10% B).

Bzls-D-Phe(4-AMe)-Phe(4-AMe)-4-cyanobenzylamide.2TFA

3l

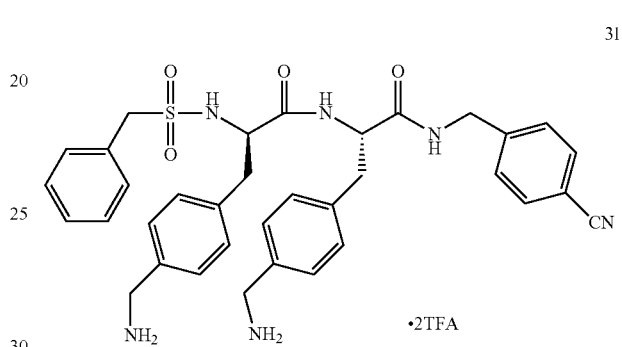

Bzls-D-Phe(4-Tfa-AMe)-Phe(4-Tfa-AMe)-4-cyanobenzylamide (3k), (1.6 g, 1.93 mmol) was dissolved in 12 ml dioxane and 12 ml (12 mmol) 1N NaOH solution and stirred for 3 h at 45° C. The mixture was neutralized by addition of 1N HCl. The solvent was removed in vacuo, the residue dissolved in 30% solvent B and the product purified by preparative HPLC (start of the gradient at 15% B). The product containing fractions were combined, the solvent was partially removed in vacuo, and the product was lyophilized. Yield: 865.2 mg 3l as a white lyophilized solid (HPLC: 23.6 min, purity 95.2% at 220 nm, start at 10% B, MS: calc.: 638.27 found: 639.38 (M+H)$^+$).

3m

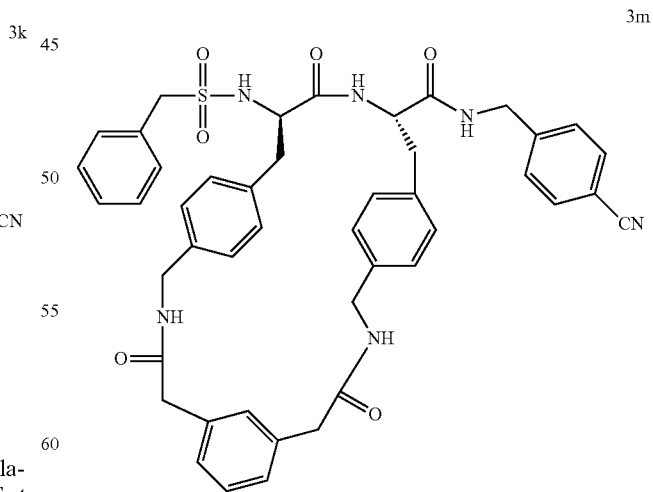

m-Phenylenediacetic acid (34 mg, 0.173 mmol) was dissolved in 60 ml DMF and treated with 131.5 mg (0.346 mmol) HBTU and 60.2 µl (0.346 mmol) DIPEA and stirred on the ice bath for 15 min. The mixture was treated with 150 mg (0.173 mmol) Bzls-D-Phe(4-AMe)-Phe(4-AMe)-4-cyanobenzylamide.2TFA and 60.2 μl (0.346 mmol) DIPEA and was stirred on the ice bath for 3 h and at room temperature for 48 h. The solvent was removed in vacuo, and the crude product 3m (504 mg) was directly used for the following step. HPLC: 41.1 min, start at 10% B, MS: calc.: 796.30 found: 797.3 (M+H)+.

Crude intermediate 3n (183 mg) was suspended in 5 ml acetic acid, and treated with 65.7 μl (0.692 mmol) acetic anhydride and stirred at room temperature for 1 h. The solvent was removed in vacuo, redissolved in 60 ml acetic acid (90%), and hydrogenated at 40° C. overnight using Pd/C as catalyst. The catalyst was removed by filtration, the solvent was evaporated and the residue dissolved in 30% solvent B and the product purified by preparative HPLC (start at 20% B). The product containing fractions were combined and lyophilized to provide 3 as a white lyophilized solid (HPLC: 28.7 min, start at 10% B, MS: calc.: 813.3 found: 814.3 (M+H)+, TLC: $R_f$=0.73).

Example 4

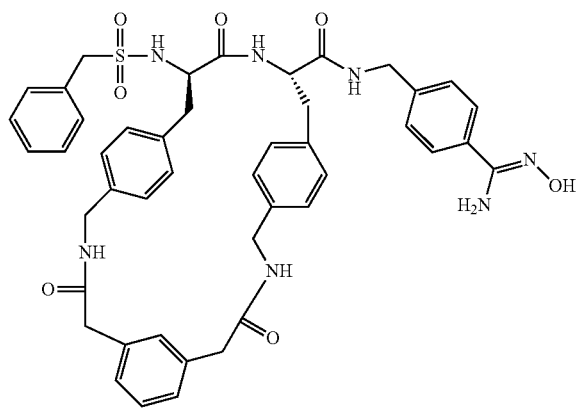

3n

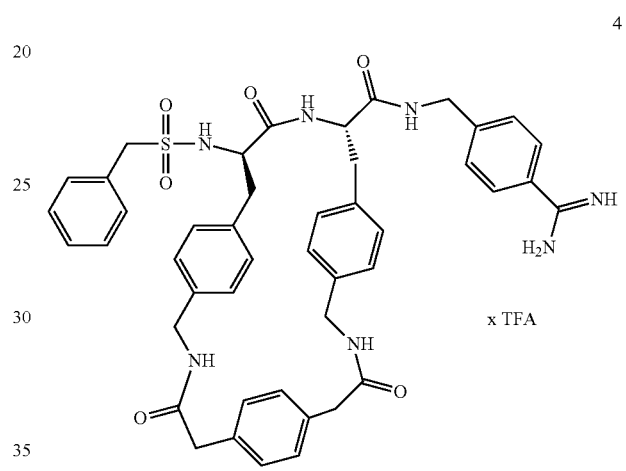

4 x TFA

Crude intermediate 3m (504 mg) was suspended in 5 ml absolute ethanol, and treated with 36.3 mg (0.519 mmol) hydroxylamine.HCl and 90.3 μl (0.519 mmol) DIPEA. The mixture was refluxed 4 h and stirred at room temperature overnight. The mixture still contained approximately 60% starting material 3m based on HPLC analysis. Therefore, the mixture was treated with additional 36.3 (0.519 mmol) hydroxylamine.HCl and 90.3 μl (0.519 mmol) DIPEA, the suspension was refluxed for 6 h and stirred at room temperature overnight. The solvent was removed in vacuo and the residue dissolved in a mixture of saturated NaHCO$_3$ solution and ethyl acetate. The organic phase was washed 3× with saturated NaHCO$_3$ solution and 3× with brine. During the washing procedure some product 3n precipitated between the phases, and was recovered by filtration. The organic phase was dried with Na$_2$SO$_4$, filtered and the solvent was removed in vacuo to provide additional product. Yield: 214 mg crude 3n as a white solid (HPLC: 28.7 min, start at 10% B). The combined materials were directly used for the next step.

Inhibitor 4 was synthesized as described above for example 3, and was obtained as a white lyophilized solid. HPLC: 18.0 min, start at 20% B, MS: calc.: 813.3 found: 814.3 (M+H)+, TLC: $R_f$=0.69.

Example 5

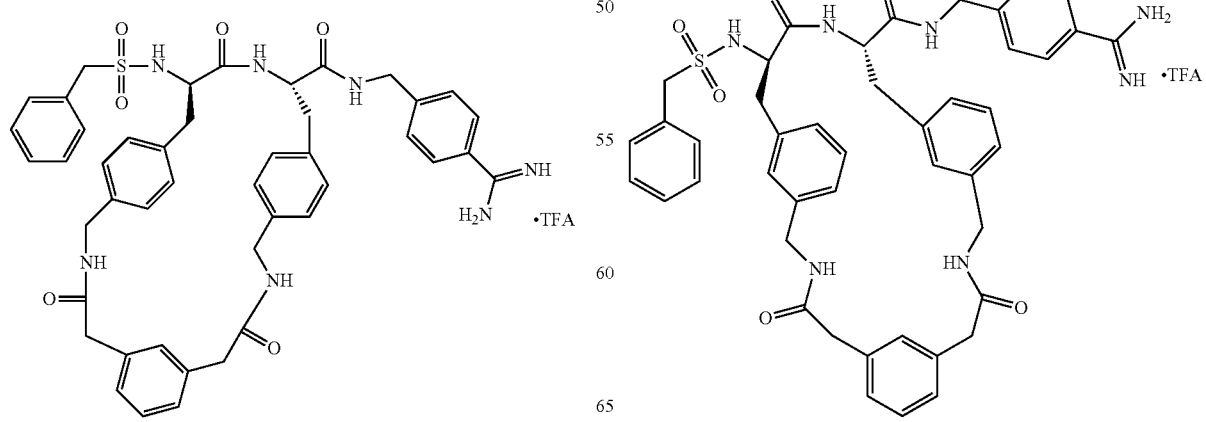

3

5

Boc-D-Phe(3-CN)—OH

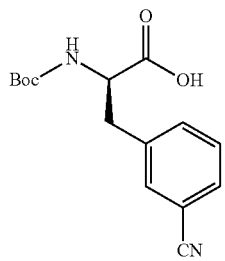

5a

H-D-Phe(3-CN)—OH (3.0 g, 13.2 mmol) was dissolved in 66 ml dioxane and 33 ml water and stirred at 0° C. The mixture was treated with 3.18 g (14.6 mmol) Boc₂O and 14.6 ml (14.6 mmol) 1 N NaOH solution, the pH was adjusted with additional 1 N NaOH solution to 8-9, and the mixture was stirred at room temperature an additional 6 h. The solvent was removed in vacuo, and the residue was dissolved in a mixture of 5% KHSO₄ solution and ethyl acetate. The water phase was extracted twice with ethyl acetate, and the combined organic phases were washed 3× with brine and dried with Na₂SO₄. The solvent was filtered and evaporated in vacuo. Yield: 3.8 g 5a as a white solid (HPLC: 31.5 min, start at 10% B).

Boc-Phe(3-CN)—OH

5b

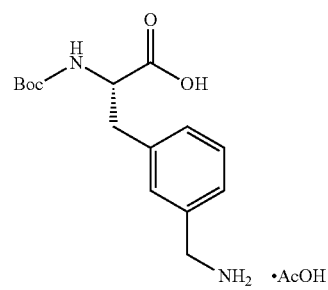

The synthesis of intermediate 5b was performed according to the procedure described for intermediate 5a. Yield: 3.2 g white solid (HPLC: 31.5 min, start at 10% B).

Boc-D-Phe(3-AMe)-OH.CH₃COOH

5c

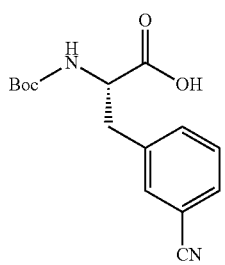

Boc-D-Phe(3-CN)—OH (5a), (3.7 g, 12.9 mmol) was dissolved in 750 ml acetic acid (90%), 10% Pd/C (374 mg) was added, and the mixture hydrogenated at 40° C. overnight. The catalyst was filtered and the solvent evaporated in vacuo. The residue was dissolved in a small amount of methanol and the product was precipitated by addition of diethyl ether. Yield: 2.7 g 5c as a white solid (HPLC: 17.8 min, start at 10% B).

Boc-Phe(3-AMe)—OH.CH₃COOH

5d

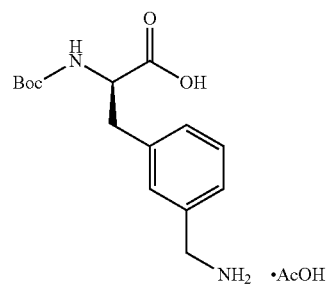

The synthesis of 5d was performed according to the procedure described for intermediate 5c, using 3.1 g (10.9 mmol) Boc-Phe(3-CN)—OH. Yield: 2.1 g white solid (HPLC: 17.8 min, start at 10% B).

Boc-D-Phe(3-AMe-Chz)-OH

5e

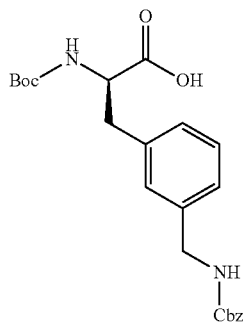

Boc-D-Phe(3-AMe)-OH.AcOH (5c), (2.7 g, 7.52 mmol) was dissolved in MeCN and stirred on the ice bath. The mixture was treated with 1.87 g (7.52 mmol) Cbz-OSu and 827 μl (7.52 mmol) NMM and was stirred overnight. The solvent was removed in vacuo and the residue was dissolved in a mixture of 5% KHSO₄ solution and ethyl acetate. The water phase was extracted 2× with ethyl acetate, the combined organic phases were washed with 5% KHSO₄ and 3× with brine, dried with Na₂SO₄, and filtered. Solvent was removed in vacuo. Yield: 3.1 g 5e as a light yellow solid (HPLC: 38.6 min, start at 10% B).

Boc-Phe(3-AMe-Cbz)-OH

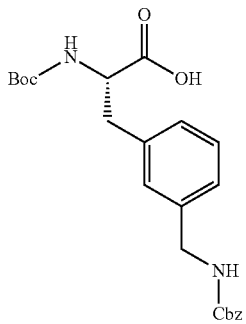

The synthesis was performed according to the procedure described for intermediate 5e, using 2.05 g (5.78 mmol) Boc-Phe(3-AMe)-OH.CH$_3$COOH. Yield: 2.45 g light yellow amorphous solid (HPLC: 38.6 min, start at 10% B).

H-D-Phe(3-AMe-Cbz)-OH.TFA

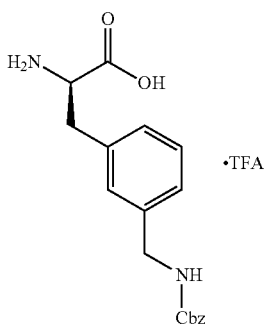

Boc-D-Phe(3-AMe-Cbz)-OH (5e) (3.1 g) was treated with 40 ml 50% TFA/CH$_2$Cl$_2$. The solvent was removed after 1 h, the residue was dissolved in water, and the solvent was evaporated. The residue was lyophilized from 40% t-butanol. Yield: 3.0 g 5g as a white lyophilized solid (HPLC: 15.3 min, start at 20% B).

Bzls-D-Phe(3-AMe-Cbz)-OH

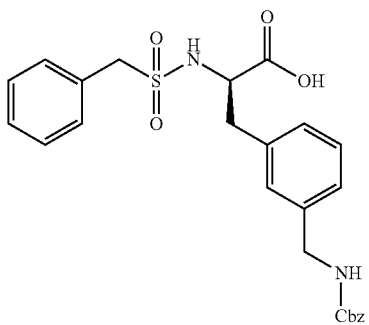

H-D-Phe(3-AMe-Cbz)-OH.TFA (5g), (3.0 g, 6.78 mmol) was suspended in 30 ml dry DCM and treated with 1850 μl (14.9 mmol) TMS-Cl and 3.8 ml (21.7 mmol) DIPEA. The mixture was refluxed for 1 h and cooled to 0° C., followed by addition, of 1.42 g (7.46 mmol) benzylsulfonyl chloride in several portions over a period of 35 min. The pH was maintained at 8-9 by addition of DIPEA (1275 μl, 7.33 mmol). The mixture was stirred on the ice bath for 1 h and at room temperature overnight.

The solvent was removed in vacuo, and the remaining brown residue was dissolved in water with 1 N NaOH solution (pH 8-9) and extracted 2× with ethyl acetate. The pH of the water phase was adjusted to 1-2 with 5% KHSO$_4$ solution and extracted 2× with ethyl acetate. The combined organic phases were washed 2× with 5% KHSO$_4$ solution and 3× with brine, dried with Na$_2$SO$_4$, filtered and the solvent removed in vacuo. The residue was dissolved in 150 ml ethyl acetate and treated with 1170 μl (10.2 mmol) cyclohexylamine. The cyclohexylamine salt of the product crystallized at 4° C. and was obtained by filtration and washed with ethyl acetate and diethyl ether and dried in vacuo. The residue was dissolved in a mixture of 5% KHSO$_4$ solution and ethyl acetate, the water phase was extracted twice with ethyl acetate. The combined organic phases were washed 2× with 5% KHSO$_4$ solution and 3× with brine, dried with Na$_2$SO$_4$, filtered and the solvent removed in vacuo. The oily residue slowly crystallized at 4° C. Yield: 2.57 g 5h as a light brown solid (HPLC: 28.7 min, start at 20% B).

Boc-Phe(3-AMe-Cbz)-OMe

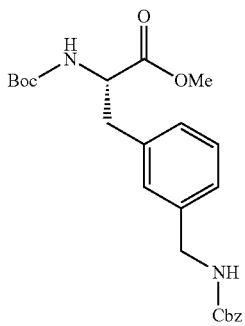

N-methyl-N-nitroso-p-toluenesulfonamide (Diazald™) (4.28 g, 20 mmol) was suspended in 25 ml diethyl ether, 6.3 ml (80 mmol) 2-methoxyethanol and some drops of water. The mixture was stirred on the ice bath and was treated dropwise with a mixture of 3.3 ml ethanol and 70% KOH solution. The solution was heated to 35-40° C., and diazomethane and ether were distilled into a solution containing 5.6 mmol Boc-Phe(3-AMe-Cbz)-OH (5f), (2.4 g in 30 ml ethanol). The excess diazomethane was degraded by addition of acetic acid, and the solvent was removed in vacuo to leave crude 3.0 g 5i as a dark yellow oil (HPLC: 43.7 min, start at 10% B).

H-Phe(3-AMe-Cbz)-OMe.TFA

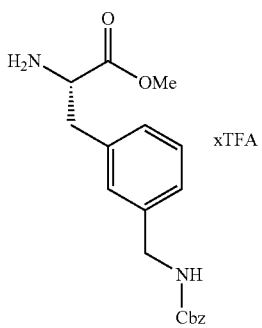

Crude intermediate 5i (3.0 g) was dissolved in 30 ml 50% TFA/CH$_2$Cl$_2$ with occasional shaking, and after 1 h the solvent was removed in vacuo. Residual acid was removed by repeatedly dissolving in water and evaporating. The residue was dissolved in 40% t-butanol/H$_2$O and lyophilized. Yield: 2.46 g 5j as a white lyophilized solid (HPLC: 26.3 min, start at 10% B).

Bzls-D-Phe(3-AMe-Cbz)-Phe(3-AMe-Cbz)-OMe

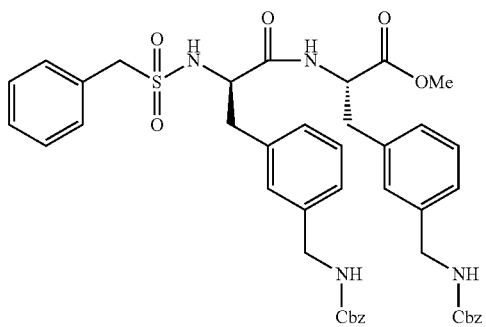

Bzls-D-Phe(3-AMe-Cbz)-OH (1.3 g, 2.69 mmol) and H-Phe(3-AMe-Cbz)-OMe (1.23 g, 2.69 mmol) were dissolved in 30 ml DMF and stirred on the ice bath. The solution was treated with 1.41 g (2.69 mmol) PyBOP and 469 μl (8.08 mmol) DIPEA (pH 7-8), and the mixture was stirred overnight. The solvent was removed in vacuo and the residual dark yellow oil was dissolved in ethyl acetate. The organic phase was washed 3× with 5% KHSO$_4$ solution, 1× with brine, 3× with saturated NaHCO$_3$ solution and 3× with brine, dried with Na$_2$SO$_4$, filtered and the solvent removed in vacuo. Yield of crude 5k: 2.7 g light yellow amorphous solid (contains some impurities; HPLC: 52.0 min, start at 20% B).

Bzls-D-Phe(3-AMe)-Phe(3-AMe)-OMe.2TFA

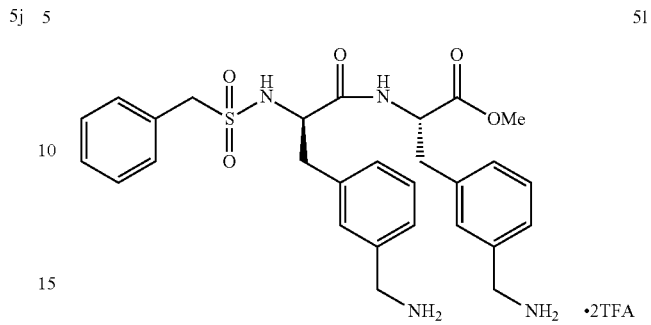

Crude Bzls-D-Phe(3-AMe-Cbz)-Phe(3-AMe-Cbz)-OMe (5k) (2.7 g) was treated with 30 ml 32% HBr in acetic acid with occasional shaking. After 1.5 h at room temperature the product was precipitated by addition of diethyl ether, filtered and dried in vacuo. The light yellow solid was dissolved in 30% solvent B and the product purified by preparative HPLC (start at 15% B). The product containing fractions were combined, the solvent partially removed in vacuo, and the product was lyophilized. Yield: 1.33 g 5l as a white lyophilized solid (HPLC: 14.7 min, start at 20% B, MS: calc.: 538.22 found: 539.34 (M+H)$^+$.)

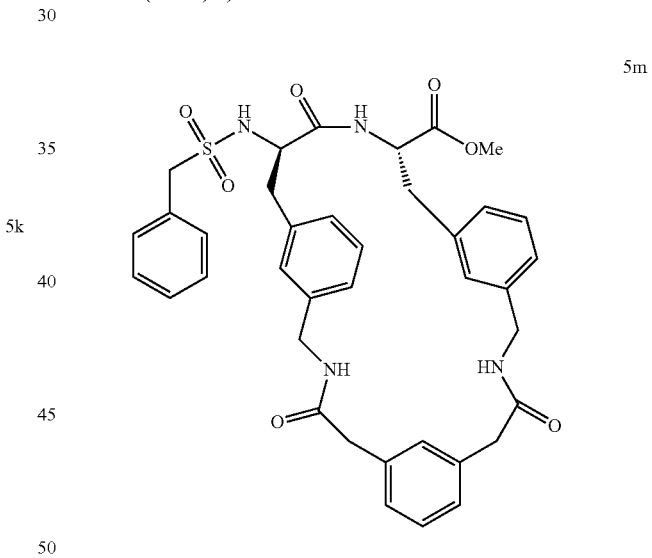

Bzls-D-Phe(3-AMe)-Phe(3-AMe)-OMe.2TFA (5l), (50 mg, 0.0652 mmol) and m-phenylenediacetic acid (12.7 mg, 0.0652 mmol) were dissolved in 30 ml DMF. The mixture was stirred on the ice bath and treated with 68 mg (0.130 mmol) PyBOP and 68.1 μl (0.391 mmol) DIPEA. The solvent was removed in vacuo, and the residue dissolved in a mixture of 5% KHSO$_4$ solution and ethyl acetate. The organic phase was washed 3× with 5% KHSO$_4$ solution, 1× with brine, 3× with saturated NaHCO$_3$ solution and 3× with brine. The organic phase was dried with Na$_2$SO$_4$, filtered and the solvent removed in vacuo. Yield of crude product 5m: 66 mg white amorphous solid (contains impurities, HPLC: 36.2 min, start at 10% B).

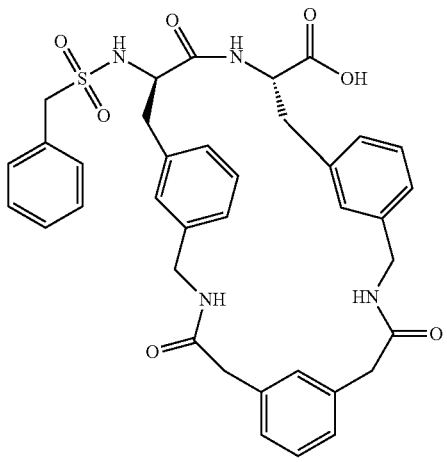

5n

Crude product 5m (61 mg) was suspended in 4 ml ethanol and 4 ml water, treated with 283 µl N NaOH, and stirred at room temperature for 2 h. The solvent was removed in vacuo, and the residue was dissolved in a mixture of 5% KHSO$_4$ solution and ethyl acetate. The water phase was extracted 2× with ethyl acetate, the combined organic phase was washed 1× with 5% KHSO$_4$ solution, and 3× with brine. The organic phase was dried with Na$_2$SO$_4$, filtered and the solvent evaporated in vacuo. Yield of crude 5n: 57.7 mg white amorphous solid (contains some impurities, HPLC: 33.5 min, start at 10% B).

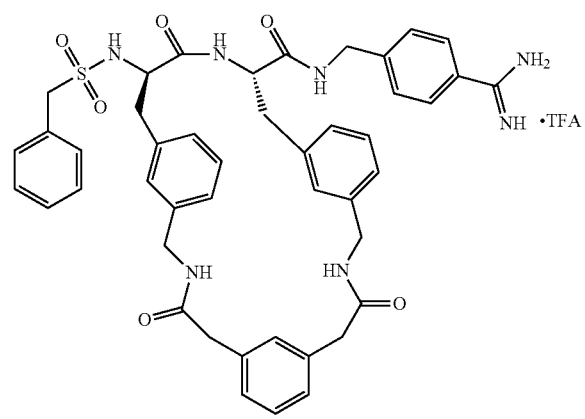

5

Crude product 5n (53 mg, ca. 0.0652 mmol) and 4-Amba.2HCl (14.5 mg, 0.0652 mmol) were suspended in 20 ml DMF. The mixture was stirred on an ice bath, treated with 34 mg (0.0652 mmol) PyBOP and 22.7 µl (0.130 mmol) DIPEA, and stirred overnight. The solvent was removed in vacuo, the remaining yellow oily residue was dissolved in 40% solvent B, and the product was purified by preparative HPLC (start at 25% B). The product-containing fractions were combined, the solvent partially removed in vacuo and the product lyophilized. Yield: 15.3 mg white lyophilzed solid (HPLC: 20.8 min, start at 20% B, MS: calc.: 813.33 found: 814.6 (M+H)$^+$, TLC: R$_f$=0.70).

Example 6

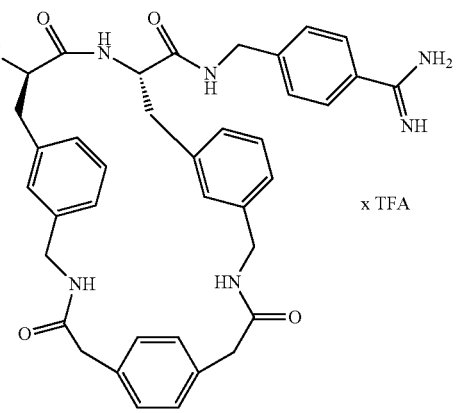

6

Inhibitor 6 was synthesized according to the strategy used for inhibitor 5, with the intermediate 5l being cyclised with p-phenylenediacetic acid. Yield: 13.2 mg white lyophilized solid (HPLC: 19.8 min, start at 20% B, MS: calc.: 813.33 found: 814.2 (M+H)$^+$, TLC: R$_f$=0.68).

Example 7

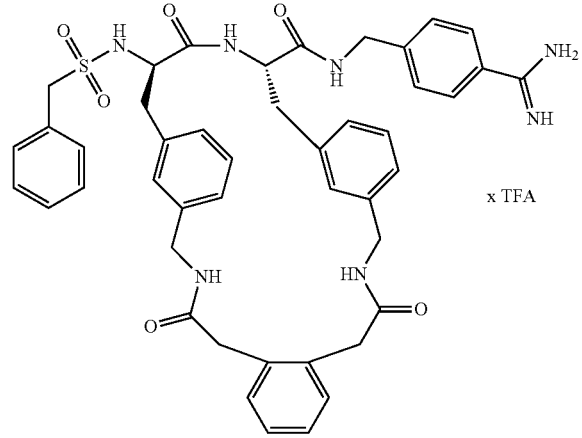

7

Inhibitor 7 was synthesized according to the strategy used for inhibitor 5, with the intermediate 5l being cyclised with o-phenylenediacetic acid. Yield: 8.9 mg white lyophilized solid (HPLC: 23.2 min, start at 20% B, MS: calc.: 813.3 found: 814.1 (M+H)$^+$, TLC: R$_f$=0.65).

Example 8

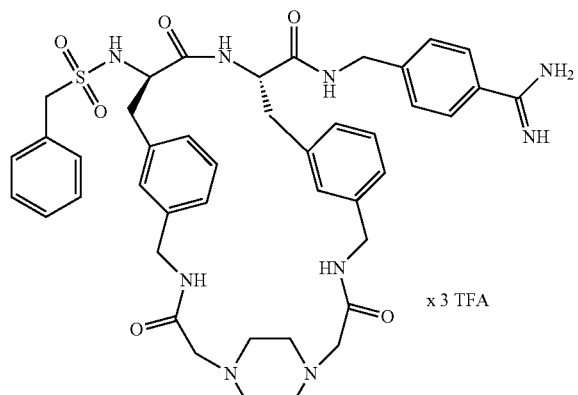

N,N'-piperazinediacetic acid

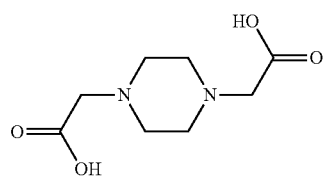

Piperazine (1 g, 11.6 mmol) was dissolved in 10 ml 10% NaOH solution, treated with 3.32 g (23.8 mmol) bromoacetic acid and stirred at room temperature. After 3 h, the mixture was acidified with 37% HCl solution, and the product started to crystallize. The flask was kept at 4° C. overnight, the product was obtained by filtration, washed with a small amount of water and was dried in vacuo. Yield: 2.28 g white crystals (MS: calc.: 202.2. found: 203.0 (M+H)$^+$; $^1$H-NMR (400 MHz, D$_2$O): δ [ppm] 3.85 4H, s, 2×CH$_2$; 3.59 8H, s, 4×CH$_2$).

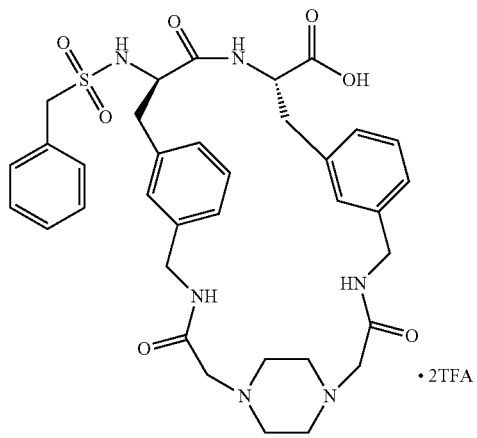

Bzls-D-Phe(3-AMe)-Phe(3-AMe)-OMe.2TFA (5l) (50 mg, 0.0652 mmol) and N,N'-piperazinediacetic acid (13.2 mg, 0.0652 mmol) were suspended in 35 ml DMF at 0° C. The suspension was treated with 68 mg (0.130 mmol) PyBOP and 68.1 μl (0.391 mmol) DIPEA and stirred at room temperature overnight. The solvent was removed in vacuo, and the residue dissolved in 5 ml ethanol/water (1/1, v/v)) and treated with 210 μl N NaOH. The mixture was stirred at room temperature for 2 h and then neutralized by addition of TFA. The solvent was removed in vacuo, the white residue dissolved in 35% solvent B and the product purified by preparative HPLC (start at 15% B). The product containing fractions were combined, the solvent was partially evaporated, the residue was dissolved in 80% t-butanol/water, and the product was lyophilized. Yield: 22.4 mg 8b as a white lyophilized solid (HPLC: 27.4 min, start at 10% B, MS: calc.: 690.28 found: 691.31 (M±H)$^+$).

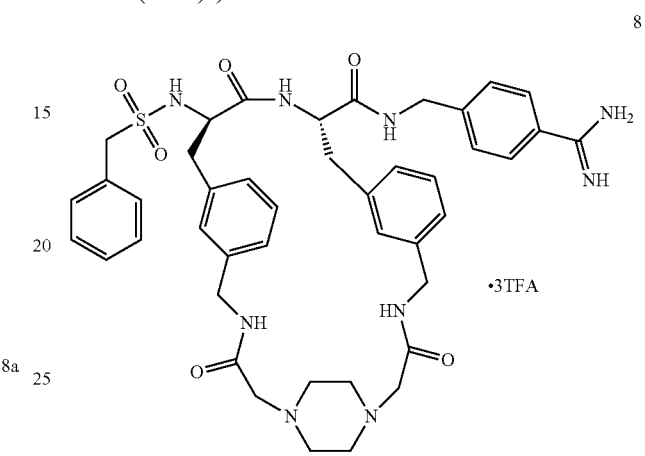

Intermediate 8b (20 mg, 0.0290 mmol) and 4-Amba.2HCl (6.8 mg, 0.0306 mmol) were suspended in 10 ml DMF and stirred on the ice bath. The mixture was treated with 15.1 mg (0.0290 mmol) PyBOP and 10.1 μl (0.0579 mmol) DIPEA and was stirred at room temperature overnight. The solvent was removed in vacuo, and the product purified by preparative HPLC (start at 20% B). The product containing fractions were combined and the product was obtained by lyophilization from 40% t-butanol/water. Yield: 15.9 mg 8 as a white lyophilized solid (HPLC: 12.9 min, start at 20% B; MS: calc.: 821.37. found: 822.6 (M+H)$^+$; TLC: R$_f$=0.20).

Example 9

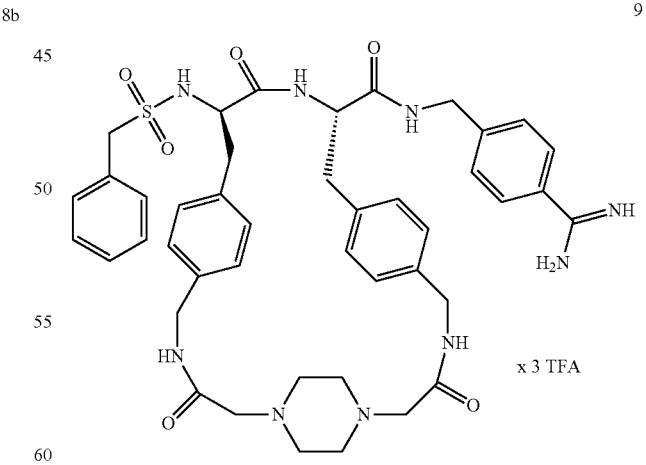

Inhibitor 9 was prepared using the strategy described for inhibitor 8. Bzls-D-Phe(4-AMe)-Phe(4-AMe)-OMe.2TFA was prepared by the method described in Example 3, and was cyclized with N,N'-piperazinediacetic acid. Yield: 18.3 mg white lyophilized solid (HPLC: 11.2 min, start at 20% B, MS: calc.: 821.37 found: 822.60 (M+H)$^+$, TLC: R$_f$=0.12).

Example 10

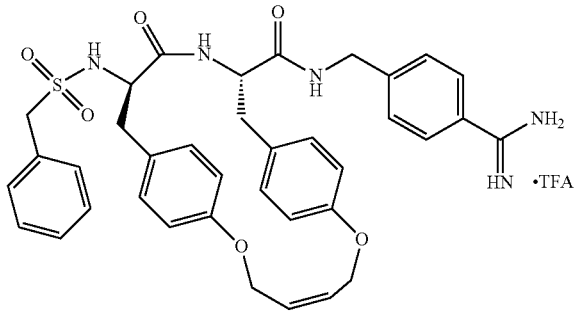

Boc-D-Tyr(All)-Tyr(All)-OMe

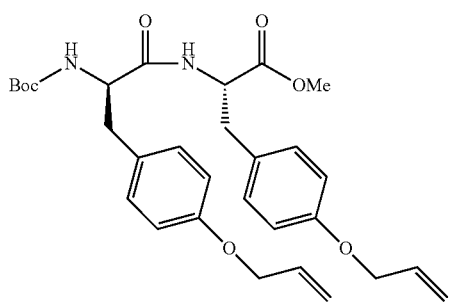
10a

Boc-D-Tyr(All)-OH (2 g, 6.22 mmol) and H-Tyr(All)-OMe (1.7 g, 6.22 mmol) were dissolved in 50 ml DMF and stirred on the ice bath. The mixture was treated with 2.36 g (6.22 mmol) HBTU and 3.25 ml DIPEA and stirred for 2 h. The solvent was removed in vacuo and the residue dissolved in a mixture of 5% $KHSO_4$ solution and ethyl acetate. The organic phase was washed 3× with 5% $KHSO_4$ solution, 1× with brine, 3× with saturated $NaHCO_3$ solution and 3× with brine, dried with $Na_2SO_4$, filtered, and the solvent removed in vacuo. Yield: 3.32 g 10a as a yellow amorphous solid (HPLC: 52.1 min, start at 10% B).

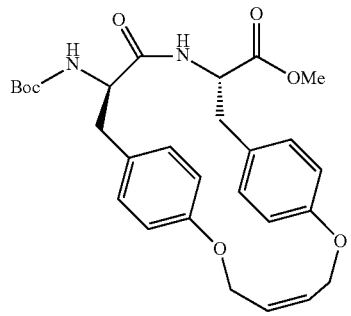
10b

Boc-D-Tyr(All)-Tyr(All)-OMe (10a), (500 mg, 0.93 mmol) was dissolved in 250 ml dry DCM under an atmosphere of argon, and was degassed for 30 min by sonication. The mixture was flushed at 40° C. (water bath) with argon for an additional 30 min. To the mixture was added 38 mg (0.0464 mmol) Grubbs I catalyst dissolved in 10 ml degassed DCM. The mixture was refluxed under an atmosphere of argon for 6 h and stirred at room temperature overnight. The solvent was removed in vacuo, the dark red residue dissolved in 40 ml acetone and treated with a small amount of silica gel 60 and evaporated. The product was purified on silica gel 60 (column 3×40 cm) using n-hexane/MTBE (1/1, v/v) as eluent. The product containing fractions were combined and the solvent evaporated. Yield: 310 mg 10b as a white solid (HPLC: 45.7 min, start at 10% B).

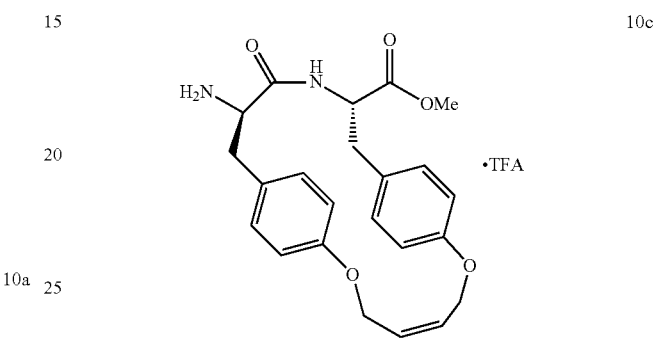
10c

Product 10b (294 mg, 0.575 mmol) was stirred with 575 µl acetic acid and 2.9 ml 1 N HCl in AcOH. The solvent was removed in vacuo after 1 h, and the light yellow residue was dissolved in 40% solvent B and purified by preparative HPLC (start at 25% B). The product containing fractions were combined and lyophilized. Yield: 265.3 mg 10c as a white lyophilized solid (HPLC: 30.7 min, start at 10% B, MS: calc.: 410.18 found: 411.04 $(M+H)^+$.

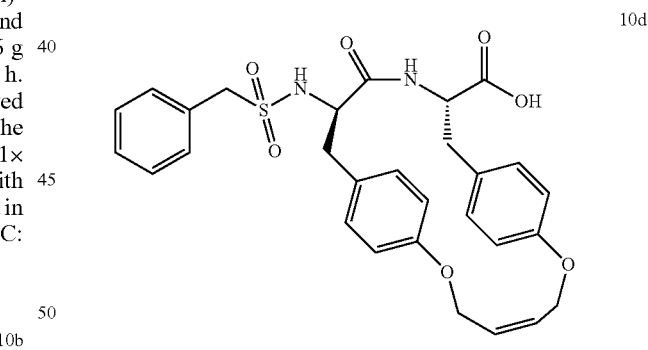
10d

Intermediate 10c (136 mg, 0.259 mmol) was dissolved in 10 ml MeCN and 3 ml water and treated with 148.3 mg Bzls-Cl in several portions, the pH being maintained at 7-8 with 1 N NaOH solution. The solvent was removed in vacuo after 4.5 h, the residue was dissolved in 10 ml dioxane and 5 ml water and treated with 5 ml 1 N NaOH solution. The mixture was stirred at 40° C. on the water bath for 1 h, neutralized by addition of TFA, and the solvent was removed in vacuo. The residue was dissolved in a mixture of 5% $KHSO_4$ solution and ethyl acetate and the water phase was extracted 3× with ethyl acetate. The combined organic phases were washed 2× with 5% $KHSO_4$ solution and 3× with brine, dried with $Na_2SO_4$, filtered and the solvent removed in vacuo. Yield: 138 mg 10d as a white amorphous solid (HPLC: 46.5 min, start at 10% B).

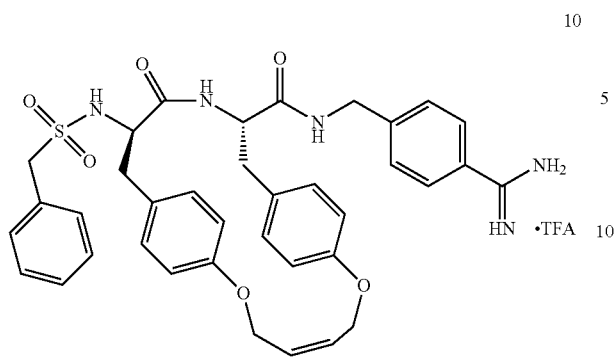

10

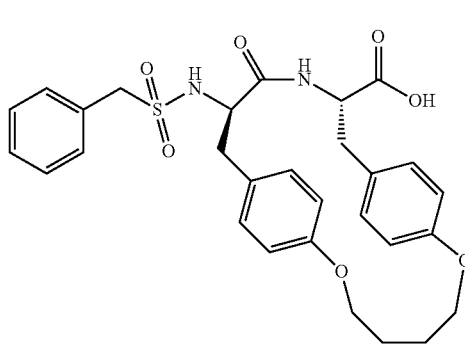

11a (40 mg) as a light gray amorphous solid (HPLC: 48.7 min, start at 10% B, MS: calc.: 552.19. found: 553.06 (M+H)$^+$, 575.04 (M+Na)$^+$).

Product 11a (30 mg, 0.0543 mmol) and 4-Amba.2HCl (14.5 mg, 0.0653 mmol) were suspended in 10 ml DMF and stirred on the ice bath. The mixture was treated with 33.8 mg (0.0653 mmol) PyBOP and 18.8 µl (0.108 mmol) DIPEA and was stirred at room temperature overnight. The solvent was removed in vacuo, the residue dissolved in 50% solvent B and filtered through a 0.2 µm membrane filter. The product containing filtrate was purified by preparative HPLC (start at 35% B). The product containing fractions were combined and lyophilized to provide 11. Yield: 30.1 mg white lyophilized solid (HPLC: 21.5 min, start at 30% B, MS: calc.: 683.82. found: 684.43 (M+H)$^+$, TLC: $R_f$=0.79).

Additional inhibitors were prepared using the methods described above, along with standard procedures common in peptide chemistry, according to the strategies described below.

Intermediate 10d (60 mg, 0.109 mmol) and 4-Amba.2HCl (36.5 mg, 0.164 mmol) were suspended in 25 ml DMF and stirred on the ice bath. The mixture was treated with 113.5 mg (0.218 mmol) PyBOP and 95 µl (0.545 mmol) DIPEA and was stirred at room temperature overnight. The solvent was removed in vacuo, the yellow residue dissolved in 50% solvent B and the product purified by preparative HPLC (start at 30% B). The product containing fractions were combined, the solvent was removed in vacuo, replaced with 80% t-butanol/water and the product lyophilized. Yield: 80.4 mg 10 as a white lyophilized solid (E/Z-mixture, HPLC: 38.2/38.5 min, start at 10% B, MS: calc.: 681.26 found: 682.13 (M+H)$^+$, TLC: $R_f$=0.78).

Example 11

Example 12

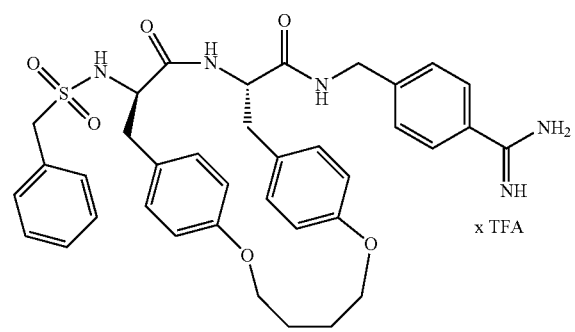

11

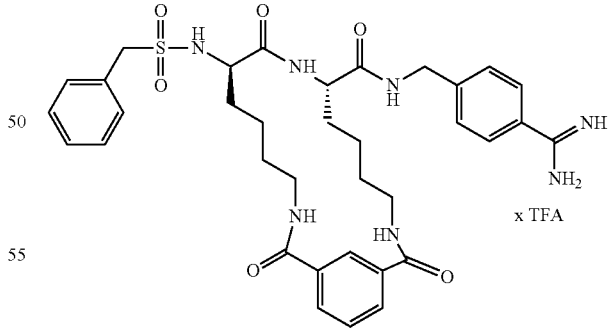

12

Intermediate 10d (55 mg, 0.10 mmol) was dissolved in 110 ml ethyl acetate, treated with 5.8 mg 10% Pd/C and the mixture was hydrogenated at room temperature for 3 h. The catalyst was removed by filtration and the solvent was evaporated to provide 11a Benzylsulfonyl-D-Lys-Lys-4-cyanobenzylamide was prepared by standard procedures. By the procedure set forth in Scheme 4 below, inhibitor 12 was obtained as a white lyophilized solid (HPLC: 22.8 min, start at 10% B, MS: calc.: 689.3. found: 690 (M+H)$^+$, TLC: $R_f$=0.54).

Scheme 4
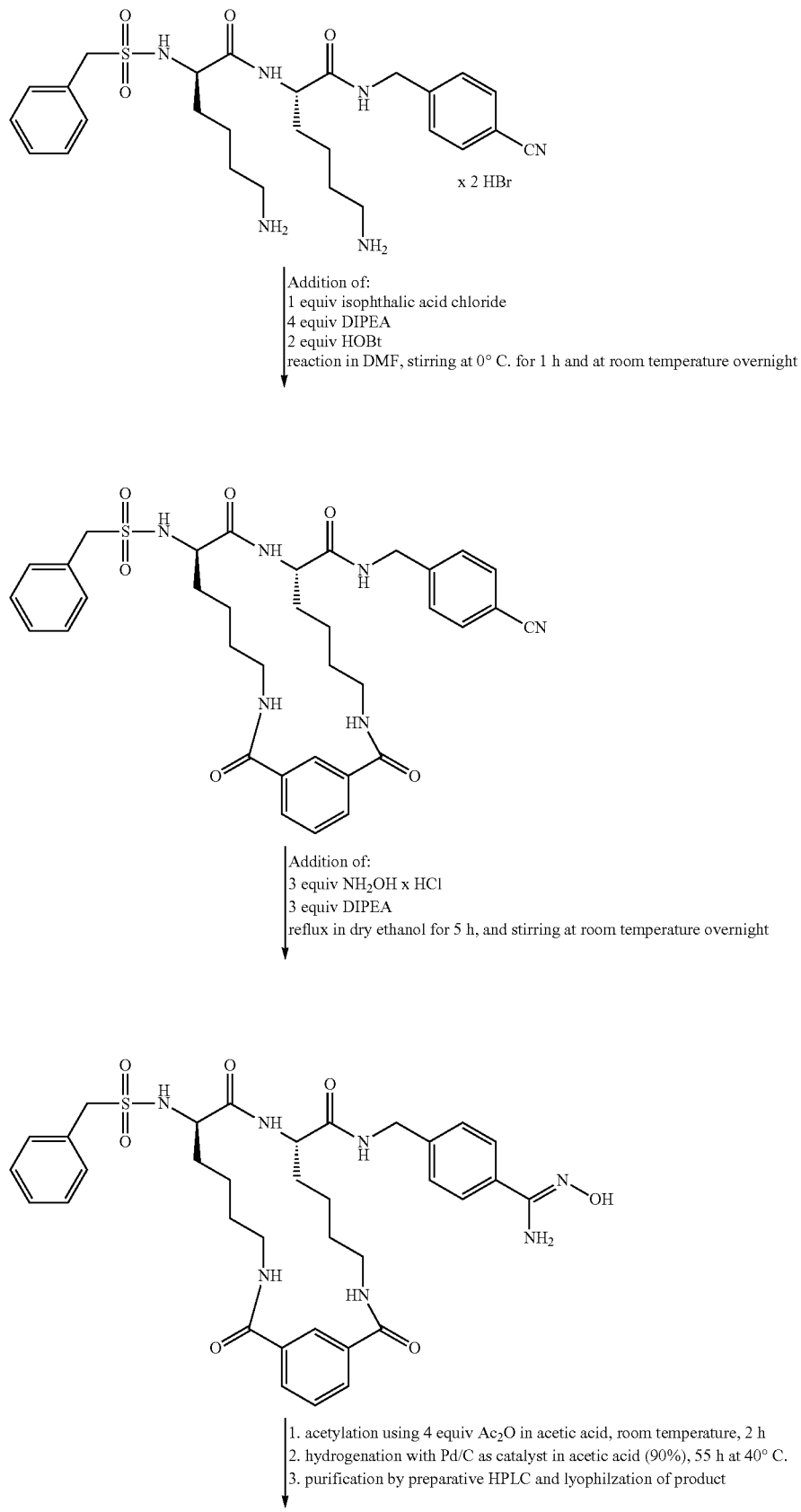

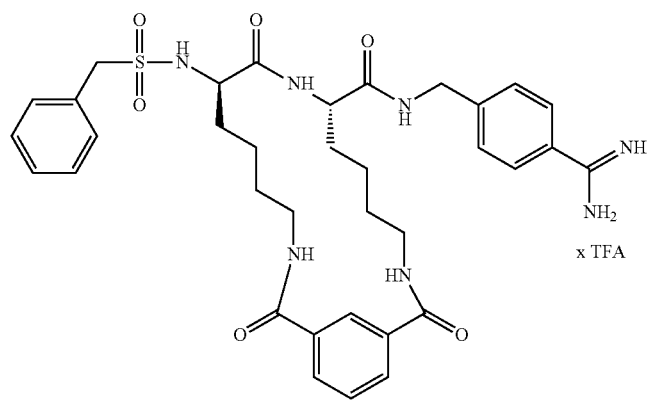 [SMILES: N=C(N)c1ccc(CNC(=O)[C@@H]2CCCCNC(=O)c3cccc(c3)C(=O)NCCCC[C@@H](NS(=O)(=O)Cc3ccccc3)C(=O)N2)cc1]

Example 13

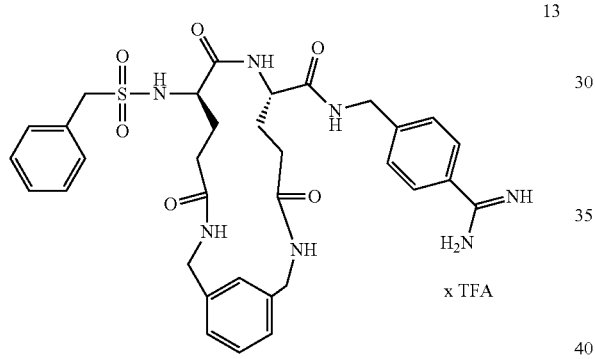

13 x TFA

The intermediate benzylsulfonyl-D-Glu-Glu-4-cyanobenzylamide was synthesized by standard procedures. Inhibitor 13 was obtained as a white lyophilized solid, (HPLC: 23.2 min, start at 10% B, MS: calc.: 661.3. found: 662 (M+H)$^+$, TLC: R$_f$=0.46) according to Scheme 5 below:

Scheme 5

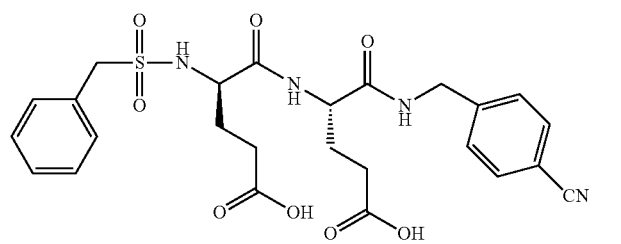

Addition of:
1.5 equiv m-xylenediamine
3 equiv DIPEA
3 equiv PyBOP
in DMF, stirring on ice bath 1 h and at room temperature overnight -continued
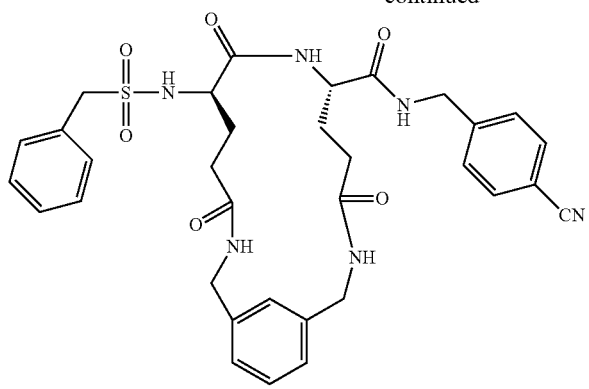
Addition of:
9 equiv NH₂OH x HCl and 9 equiv DIPEA in several portions
reflux in dry ethanol 6 h, stirring at room temperature overnight
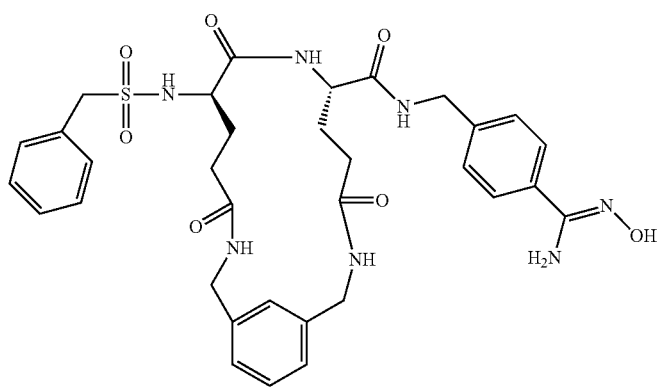
1. acetylation with 4 equiv Ac₂O in acetic acid, 2 h at room temperature
2. hydrogenation with Pd/C as catalyst in acetic acid (90%), 55 h at 40° C.
3. purification by preparative HPLC and lyophilzation of product
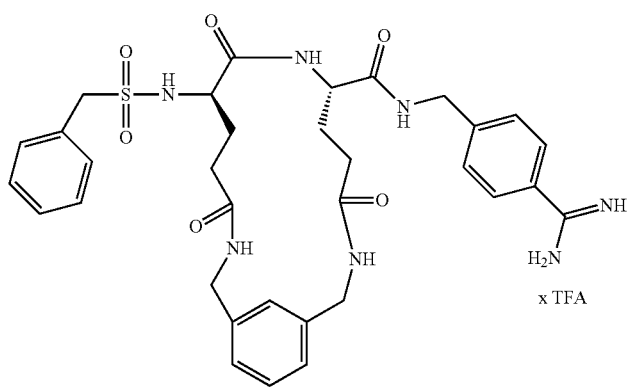 [SMILES: N=C(N)c1ccc(CNC(=O)[C@@H]2CCC(=O)NCc3cccc(c3)CNC(=O)CC[C@@H](NS(=O)(=O)Cc3ccccc3)C(=O)N2)cc1]
x TFA

Example 14

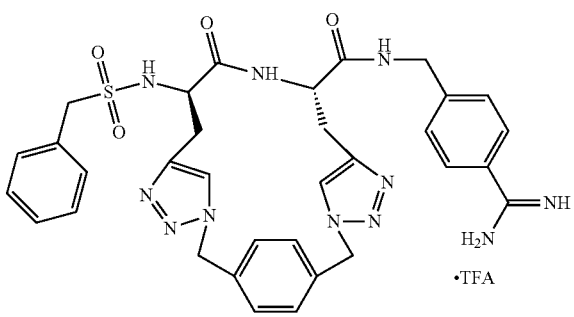

Inhibitor 14 was synthesized according to the procedure described for inhibitor 1 by using 1,4-bis(azidomethyl)benzene for the cyclization step. Inhibitor 14 was obtained as a white lyophilized solid after preparative HPLC (HPLC: 34.06 min, start at 10% B, MS: calc.: 681.3. found: 682.4 (M+H)$^+$).

Example 15

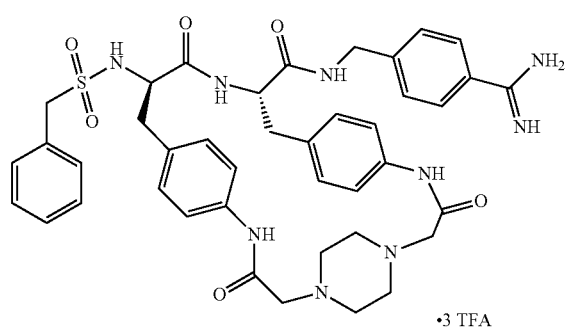

Bzls-D-Phe(4-NO$_2$)—OH

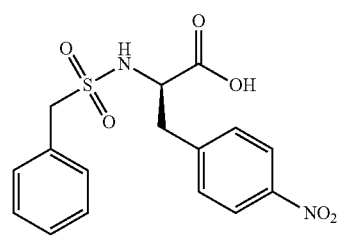

H-D-Phe(4-NO$_2$)—OH (Peptech) (5.0 g, 23.8 mmol) was suspended in 50 ml dry DCM and treated with 6.5 ml (52.4 mmol) TMS-Cl and 9.1 ml (52.4 mmol) DIPEA. The mixture was refluxed for one hour and then cooled to 0° C. The mixture was treated with 5.02 g (26.3 mmol) benzylsulfonyl chloride in several portions within 60 minutes, while the pH was maintained at 8-9 by addition of DIPEA (4.6 ml, 26.4 mmol). The mixture was stirred for 1 h at 0° C. and at room temperature overnight. The solvent was removed in vacuo and the remaining residue was dissolved in a mixture of 5% aq. KHSO$_4$ and ethyl acetate. The water phase was extracted twice with ethyl acetate, and the combined organic phases were washed 3× with 5% KHSO$_4$ and 3× with brine. The mixture was dried over Na$_2$SO$_4$, filtrated and the solvent removed in vacuo.

The remaining oily residue was dissolved in 250 ml ethyl acetate and treated with 7.1 ml (35.5 mmol) dicyclohexyl amine. The mixture was kept at 4° C. for several days. The brown crystals that formed were isolated by filtration, washed with ethyl acetate and diethyl ether, and dried in vacuo. Yield: 8.2 g light brown crystals as DCHA-salt, HPLC: 38.7 min, start at 10% B.

2.695 g of this DCHA-salt were dissolved in 5% aq. KHSO$_4$ and ethyl acetate. The acidic water phase was extracted 3× with ethyl acetate, the combined organic phases were washed 3× with brine, dried with MgSO$_4$ and filtered. The solvent was removed in vacuo. Yield: 1.80 g light brown oil, HPLC: 38.7 min, start at 10% B, MS: calc.: 364.07. found: 363.1 (M−H)$^-$.

15b) Bzls-D-Phe(4-NO$_2$)-Phe(4-NO$_2$)—OMe

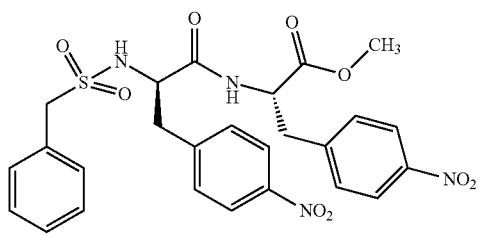

Bzls-D-Phe(4-NO$_2$)—OH (15a) (1.80 g, 4.94 mmol) and 1.288 g (4.94 mmol) H-Phe(4-NO$_2$)—OMe (Aldrich) were dissolved in 30 ml DMF and stirred on the ice bath. The mixture was treated with 2.571 g (4.94 mmol) PyBOP and 1.72 ml (9.88 mmol) DIPEA (pH 7-8). The mixture was stirred for 15 min on the ice bath and 3 h at room temperature. The solvent was removed in vacuo and the remaining dark yellow oil was treated with 5% KHSO$_4$ solution and ethyl acetate. The organic phase was washed 3× with 5% KHSO$_4$, 1× with brine, 3× with saturated NaHCO$_3$ and 3× with brine. The organic phase was dried with MgSO$_4$, filtered, and the solvent removed in vacuo. Yield: 3.55 g brown amorphous solid, containing some impurities, HPLC: 48.40 min, start at 10% B, MS: calc.: 570.57. found: 571.23 (M+H)$^+$.

Bzls-D-Phe(4-NH$_2$)-Phe(4-NH$_2$)—OMe.2TFA

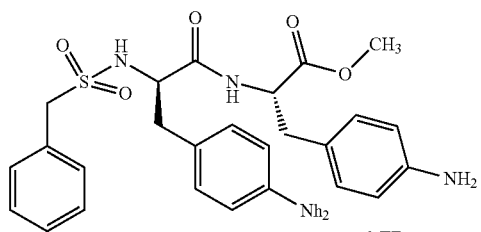

Bzls-D-Phe(4-NO$_2$)-Phe(4-NO$_2$)—OMe (15b) (2.819 g) was dissolved in 500 ml 90% acetic acid and treated with zinc dust. The mixture was stirred for 4 hours at room temperature and the solvent was removed in vacuo. The yellow residue was treated with acetonitrile/water (9/1, v/v), insoluble salts were removed by centrifugation, and the solvent was removed in vacuo. The product was purified by preparative reversed phase HPLC (column B, start at 5% solvent B) and the product-containing fractions were combined and lyophilized. Yield: 2.018 g slightly yellow lyophilized solid, HPLC: 25.01 min, start at 1% B, MS: calc.: 510.61. found: 511.27 (M+H)+.

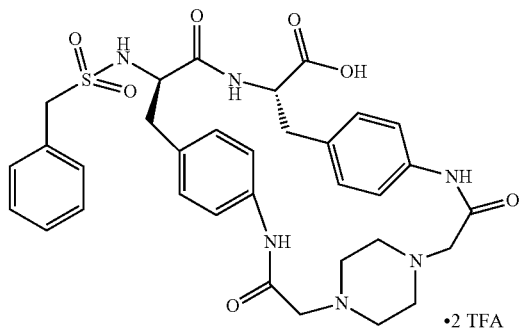

15d

Bzls-D-Phe(4-NH$_2$)-Phe(4-NH$_2$)—OMe (15e), (150 mg, 0.294 mmol) and 59.4 mg (0.294 mmol) piperazine-N,N-diacetic acid were dissolved in 150 ml DMF. The mixture was stirred on the ice bath and treated with 306.7 µl (1.76 mmol) DIPEA (pH 8), 308.3 mg PyBOP (0.588 mmol) and stirred overnight at room temperature. The solvent was removed in vacuo, the remaining residue was dissolved in ethyl acetate and was washed 2× with small amounts of saturated NaHCO$_3$ and 3× with brine. The organic phase was dried with MgSO$_4$, filtered and the solvent was removed in vacuo. The remaining residue was dissolved in a mixture of 5 ml water and 5 ml ethanol. The mixture was treated with 360 µl 1N NaOH and was stirred for 2 h at room temperature. The solution was neutralized by addition of TFA and the solvent was removed in vacuo.

The product was purified by preperative HPLC (column B, start at 15% solvent B) and the product containing frations were combined and lyophilized. Yield: 63 mg lyophilized solid, HPLC: 11.3 min, start at 20% B, MS: calc.: 662.25 found: 663.4 (M+H)+.

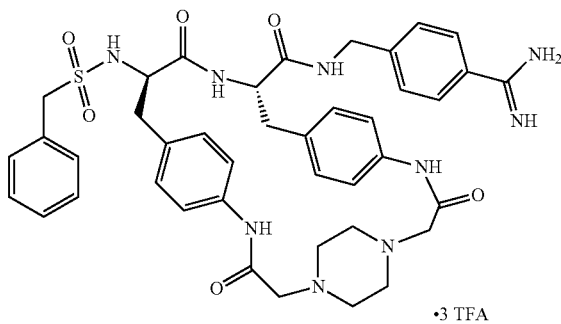

15

Intermediate 15d (54 mg, 0.048 mmol) was dissolved in 1.5 ml DMF, cooled to −15° C. and treated with 5.28 µl NMM (0.048 mmol) and 6.24 µl isobutyl chloroformate (0.048 mmol). The mixture was stirred for 10 min, followed by treatment with 6.0 mg (0.072 mmol) 4-amidinobenzylamine.2HCl and 5.28 µl (0.048 mmol) NMM. The mixture was stirred 1 h at −15° C. and at room temperature overnight. The solvent was removed in vacuo and the residue was purified by preparative HPLC (column B, start at 10% B). The product-containing fractions were combined and lyophilized. Yield: 30.8 mg white lyophilized solid, HPLC: 18.66 min, start at 10% B, MS: calc.: 793.93. found: 794.51 (M+H)+, TLC: R$_f$=0.66.

Example 16

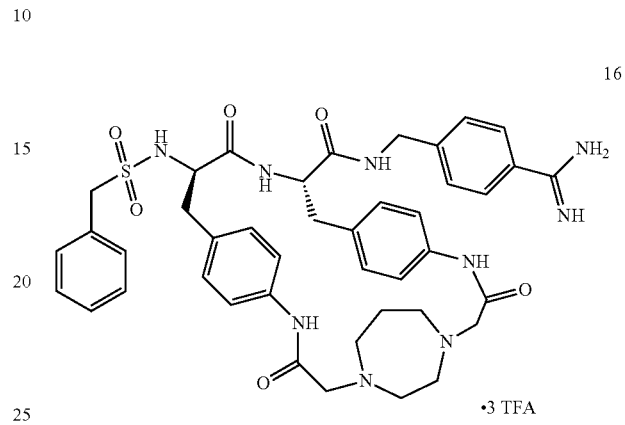

16

Compound 16 is prepared by the method described above for compound 15, but using N,N'-homopiperazinediacetic acid (prepared from homopiperazine by the method used to prepare N,N'-piperazinediacetic acid, compound 8a.)

Example 17

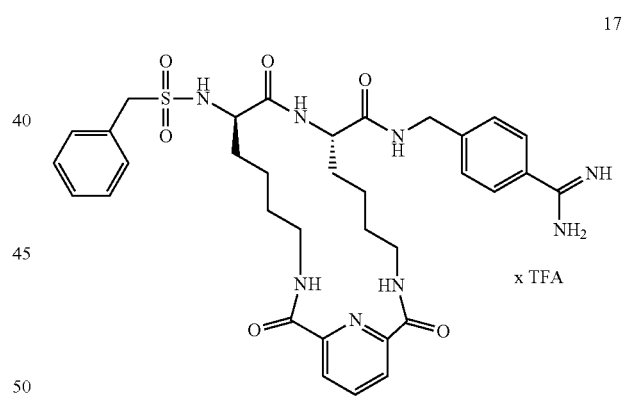

17

By the procedure set forth in Scheme 4, but using pyridine-2,6-dicarboxylic acid chloride, benzylsulfonyl-D-Lys-Lys-4-cyanobenzylamide is converted to compound 17.

Enzyme Assays

The inhibition constants for human plasmin (h plasmin), human plasma kallikrein (h PK), thrombin and factor Xa were determined in analogy to a previously disclosed method (Stürzebecher et al., *J. Med. Chem.*, 40, 3091-3099 (1997)), using a microplate reader (Multiscan Ascent™, Thermo Scientific) at 405 nm. The reactions to determine the inhibition of human plasmin and human plasma kallikrein were carried out at 25° C. in 200 µl 50 mM Tris×HCl buffer pH 8.0 (containing 0.154 M NaCl, 2% ethanol and inhibitor in appropriate concentrations) and 25 µl substrate solution. Reactions were started by addition of 50 µl of enzyme solution.

The measurements were stopped by addition of 25 μl 50% acetic acid and the $K_i$ values were calculated according to the method of Dixon. The $K_i$ values are the mean of at least two measurements. Enzymes and substrates used are set out in Table 1 below:

TABLE 1

| Enzyme | Substrate |
|---|---|
| plasmin (human), Chromogenix, specific activity 11 CU/mg | Tos-Gly-Pro-Lys-pNA (Chromozym PL) 4 mM (364 μM in measurement) 2 mM (182 μM in measurement) 1 mM (91 μM in measurement) |
| plasma kallikrein (human), Enzyme Research, South Bend IN | H-D-Pro-Phe-Arg-pNA (Haemochrom PK) 2 mM (182 μM in measurement) 1 mM (91 μM in measurement) 0.5 mM (45.5 μM in measurement) |
| thrombin (Rind), 1425 IE/mg | $CH_3SO_2$-D-Cha-Gly-Arg-pNA 2 mM (182 μM in measurement) 1 mM (91 μM i in measurement) 0.5 mM (45.5 μM in measurement) |
| Factor Xa (human), 200.35 IE/mg, Enzyme Research, South Bend IN | $CH_3OCO$-D-Cha-Gly-Arg-pNA (Pefachrome FXa) 2 mM (182 μM in measurement) 1 mM (91 μM in measurement) 0.5 mM (45.5 μM in measurement) |

Results for exemplary compounds of the invention are shown in Table 2.

TABLE 2

Ki values (in nM) of inhibitors

| | $K_i$ (nM) | | | |
|---|---|---|---|---|
| Inhibitor | h Plasmin | PK | Thrombin | FXa |
| 1 | 0.77 | 2.4 | 4300 | 206 |
| 2 | 2.2 | 10.1 | 4560 | 1860 |
| 3 | 0.55 | 550 | 3000 | 5700 |
| 4 | 9.4 | 868 | 6520 | 9370 |
| 5 | 1.1 | 17.4 | 26.8 | 42.1 |
| 6 | 6.9 | 136 | 45.4 | 152 |
| 7 | 20.3 | 8.9 | 575 | 103 |
| 8 | 4.9 | 31.6 | 9.1 | 26.3 |
| 9 | 9.0 | 493 | 2119 | 3472 |
| 10 | 2.5 | 9.4 | 100 | 220 |
| 11 | 1.9 | 34.2 | 510 | 2011 |
| 12 | 38 | 18 | 187 | 376 |
| 13 | 431 | 25 | 2020 | 3430 |
| 14 | 5.4 | 12 | 219 | 600 |
| 15 | 0.68 | 320 | 8400 | >10000 |

ADDITIONAL REFERENCES

The following references provide background information, which may be useful in understanding the state of the art prior to the present invention:

Ashgar et al., Biochim. Biophys. Acta 438, 250-264, 1976
Cohen et al., J. Lab. Clin. Med. 99, 76-83, 1982
Dixon, Biochem. J. 55, 170-171, 1953
Eriksson et al., J. Thromb. Haemostasis 1, 2490-2496, 2003
Fareed et al., Ann. N.Y. Acad. Sci. 370, 765-784, 1981
Francis et al., New Engl, J. Med. 349, 1703-1712, 2003
Garrett et al., Bioorg. Med. Chem. Lett. 9, 301-306, 1999
Garrett et al., J. Pept. Res. 52, 60-71, 1998
Griffin, Proc. Natl. Acad. Sci. USA 75, 1998-2002, 1978
Gustafsson et al., Nature Reviews 3, 649-659, 2004
Isobe, Blood & Vessel 12, 135-138, 1981
Kaplan, Prog. Hemostasis Thromb. 4, 127-175, 1978
Kettner et al., J. Biol. Chem. 265, 18289-18297, 1990
Kettner and Shaw, Biochemistry 17, 4778-4784, 1978
Künzel et al., Bioorg. Med. Chem. Lett., 12, 645-648, 2002
Lawson et al., Folia Haematol. (Leipzig) 109, 52-60, 1982
Muramatu et al. Hoppe-Seyler's Z. Physiol. Chem. 363, 203-211, 1982
Muramatu and Fuji, Biochim. Biophys. Acta 242, 203-208, 1971
Muramatu and Fuji, Biochim. Biophys. Acta 268, 221-224, 1972
Ohno et al., Thromb. Res. 19, 579-588, 1980
Okada et al., Bioorg. Med. Chem. Lett. 10, 2217-2221, 2000
Okada et al., Biopolymers 51, 41-50, 1999
Ratnoff, Blood 57, 55-58, 1981
Robinson and Saiah, Ann. Rep. Med. Chem. 37, 85-94, 2002
Satoh et al., Chem. Pharm. Bull. 33, 647-654, 1985
Schechter and Berger, Biochem. Biophys. Res. Comm. 27, 157-162, 1967
Silverberg and Kaplan, Blood 60, 64-70, 1982
Stürzebecher et al., Brazilian J. Med. Biol. Res., 27, 1929-1934, 1994
Stürzebecher et al., J. Med. Chem. 40, 3091-3099, 1997
Stürzebecher et al., Zbl. Pharm. Pharmakother. Lab. Diagn. 122, 240-241, 1983
Sucker H. et al., Pharmazeutische Technologic, 2nd circulation (1991), Georg Thieme Verlag, Stuttgart
Tada et al., Biol. Pharm. Bull. 24, 520-524, 2001
Teno et al. Chem. Pharm. Bull. 39, 2930-2936, 1991
Thromb. Res., Suppl. VIII, 131-141, 1988
Tsuda et al., Chem. Pharm. Bull. 49, 1457-1463, 2001
Weitz, Circulation, 110, 1-19-1-26, 2008
WO 1994/29336
WO 2000/041531
WO 2000/058346
WO 2001/096286
WO 2001/096366
WO 2002/062829
WO 2002/014349
WO 2003/076391
WO 2003/076457
DE 10212555
EP 1364960
U.S. Pat. No. 6,586,405
U.S. Pat. No. 5,786,328

We claim:
1. A compound having the following formula or a pharmaceutically acceptable salt thereof;
wherein $R^2$ is selected from the group consisting of: a branched, unbranched or cyclic alkyl group having 1 to 10 C atoms; a 5- or 6-membered heteroaromatic ring having 1-3 heteroatoms independently selected from N, S and O; an aryl group; a $CH_2$ group bearing a 5- or 6-membered heteroaromatic ring having 1-3 heteroatoms independently selected from N, S and O; and a $CH_2$ group bearing an aryl group; wherein said aryl group may have 6 or 10 C atoms, and wherein said heteroaromatic or aryl groups may be unsubstituted or substituted with 1 to 3 residues independently selected from the group consisting of —CH$_2$NH$_2$, —CN, —CF$_3$, tetrazol-5-yl, F, Cl, Br, —CO$_2$H, —CO$_2$Me, —CO$_2$Et, methyl, ethyl, propyl, and isopropyl;

wherein Z and Z' are independently selected from the group consisting of:

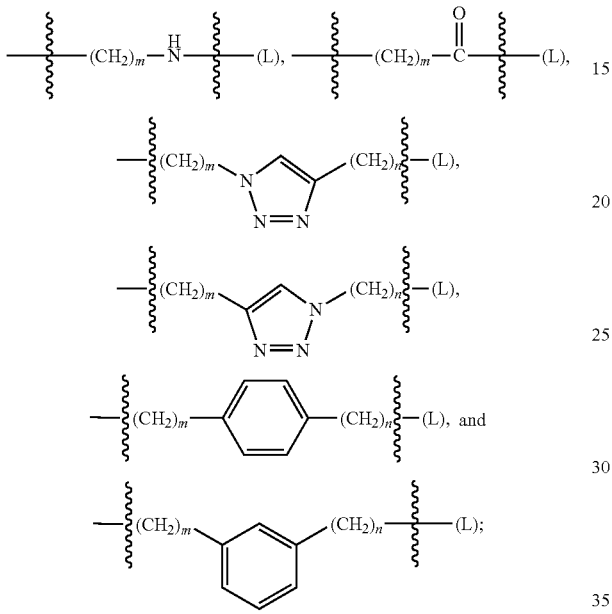

wherein the values of m and n are independently in the range 0-3; and wherein L is selected from the group consisting of:

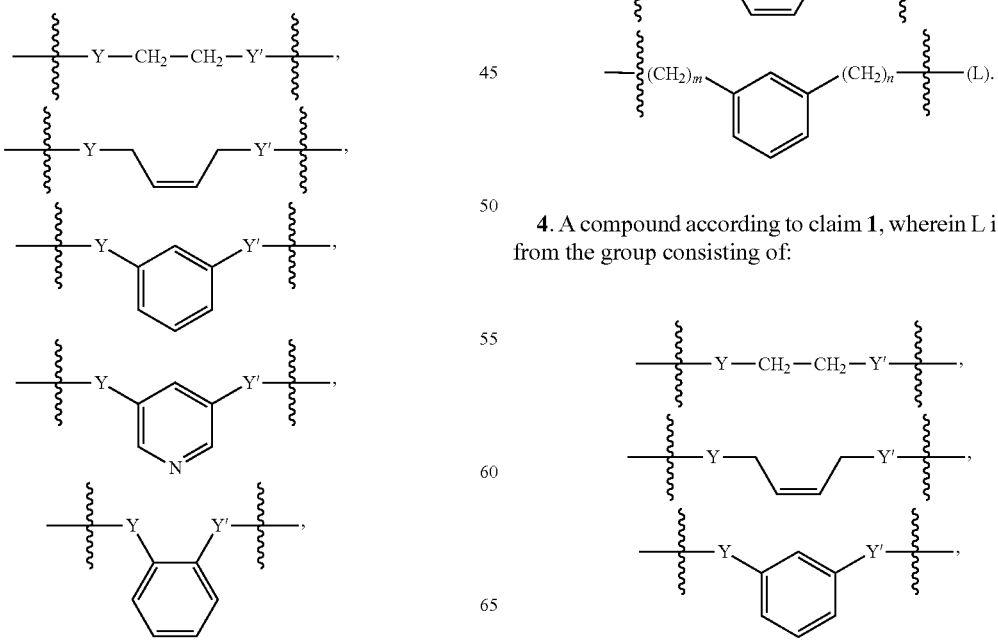

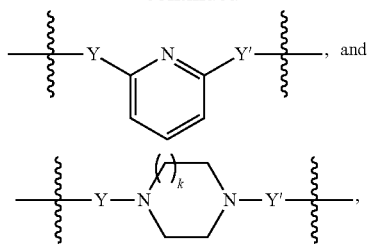

wherein k is 1 or 2, Y and Y' are independently selected from the group consisting of a covalent bond, —(CH$_2$)$_p$—, —(CH$_2$)$_p$O(OH$_2$)$_q$—, —(CH$_2$)$_p$NH (CH$_2$)$_q$—, —(CH$_2$)$_p$S(CH$_2$)$_q$—, —(CH$_2$)$_p$SS(OH$_2$)$_q$—, (CH$_2$)$_p$C(═O)(CH$_2$)$_q$—, —(CH$_2$)$_p$NHC(═O) (CH$_2$)$_q$—, —(CH$_2$)$_p$OC(═O)NH(CH$_2$)$_q$—, —(CH$_2$)$_p$ OC(═O)(CH$_2$)$_q$—, —(CH$_2$)$_p$OC(═O)NH(CH$_2$)$_q$—, —(CH$_2$)$_p$NHC(═O)—O—(CH$_2$)$_q$—, —(CH$_2$)$_p$NHC (═O)NH(CH$_2$)$_q$—, —(CH$_2$)$_p$NHC(═NH)NH (CH$_2$)$_q$—, and —(CH$_2$)$_p$NHC(═O)(CH$_2$)$_q$S—; and p and q independently range from 0 to 3.

2. A compound according to claim 1, wherein R$^2$ is a CH$_2$ group bearing an aryl group.

3. A compound according to claim 1, wherein Z and Z' are independently selected from the group consisting of:

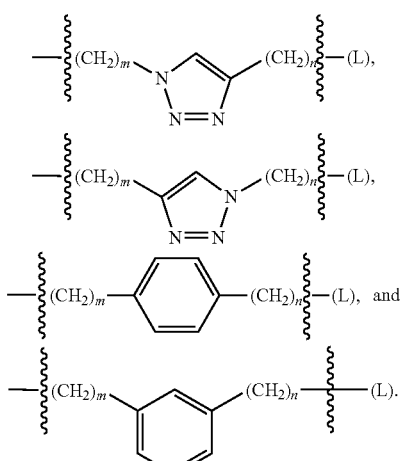

4. A compound according to claim 1, wherein L is selected from the group consisting of:

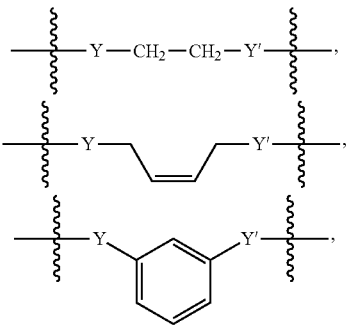

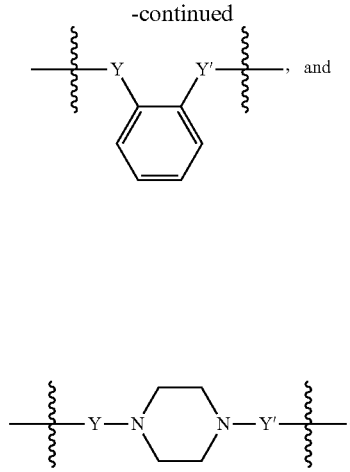

5. A pharmaceutical composition comprising one or more compounds according to claim 1, further comprising one or more pharmaceutically acceptable carriers or excipients.

6. A method for therapeutic modulation of the blood coagulation cascade or fibrinolysis, for treating a hyperfibrinolytic condition in a patient, or for controlling blood loss in a patient, said method comprising administering to a patient in need thereof an effective amount of one or more compounds according to claim 1.

7. The method of claim 6, wherein said method is to control blood loss in a patient and said patient is undergoing an organ transplant or cardiac surgical procedure or said patient is undergoing a surgical procedure with cardiopulmonary bypass.

8. A method for inhibiting plasmin alone, or plasmin and plasma kallikrein, in a patient, comprising administering to said patient an effective amount of one or more compounds according to claim 1.

9. A compound according to claim 1 for use as a medicament for the inhibition of plasmin alone, or for the inhibition of plasmin and plasma kallikrein.

10. A fibrin adhesive comprising at least one compound according to claim 1.

11. A compound according to claim 1 for use as a component of a fibrin adhesive.

12. The compound of claim 1, wherein said compound is selected from the group consisting of:

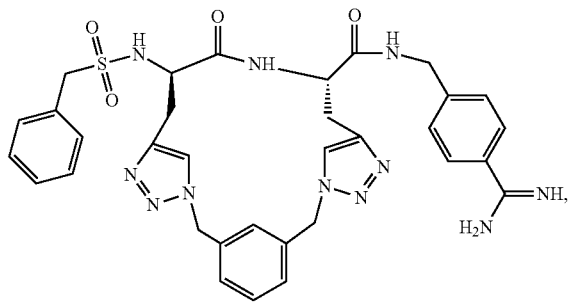

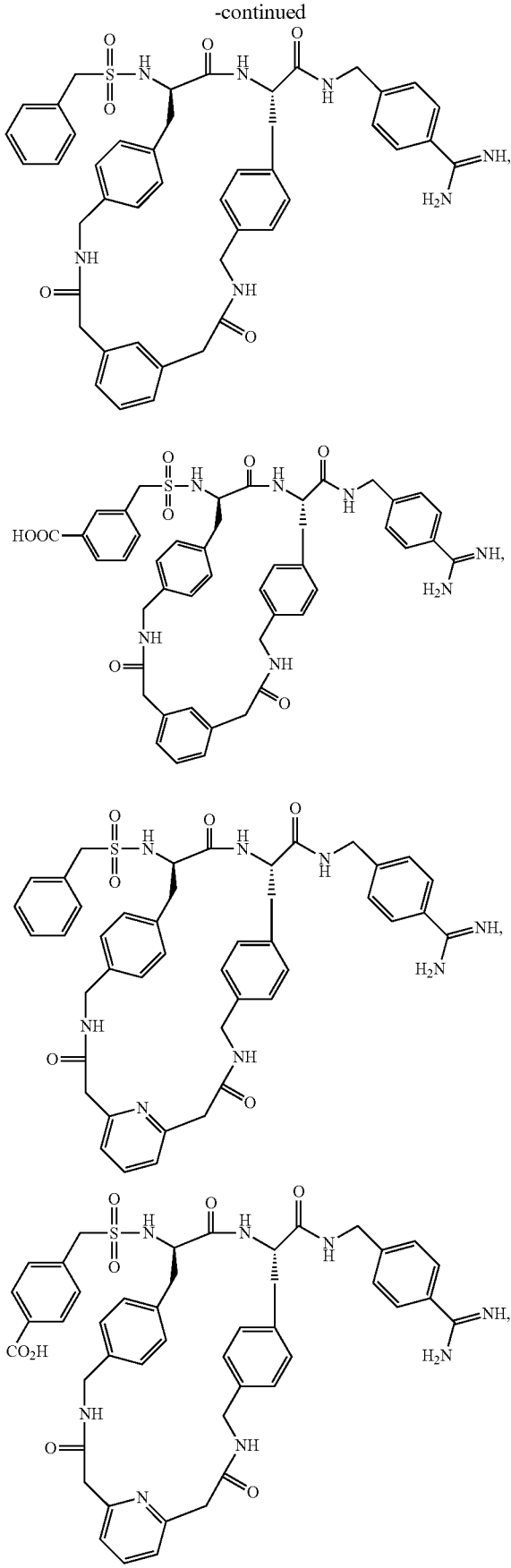

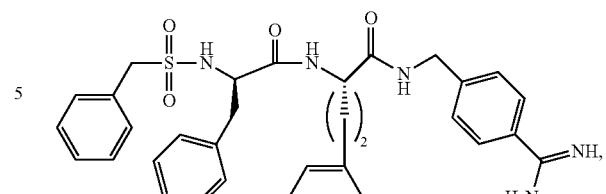
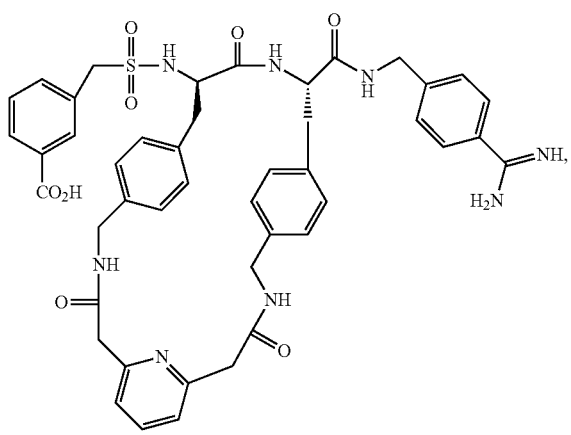
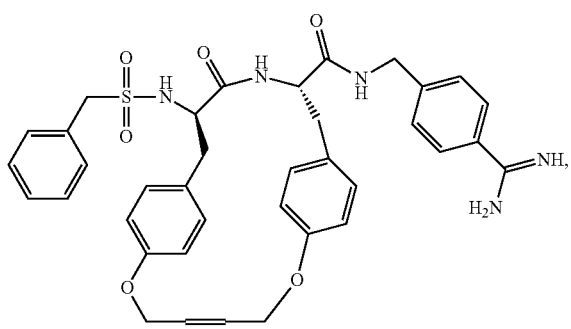
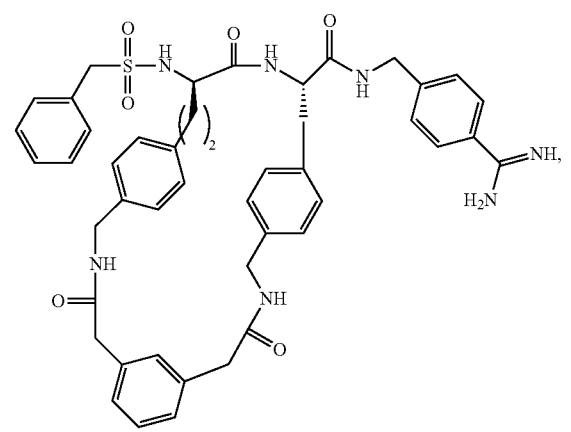
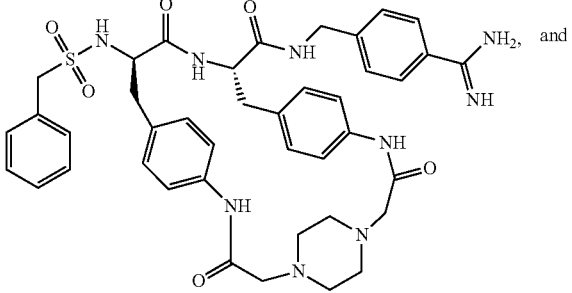
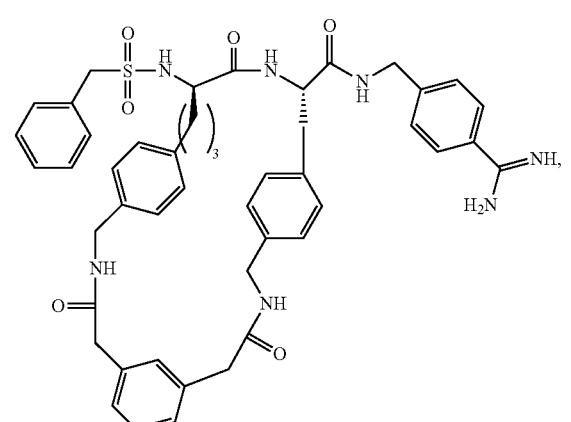
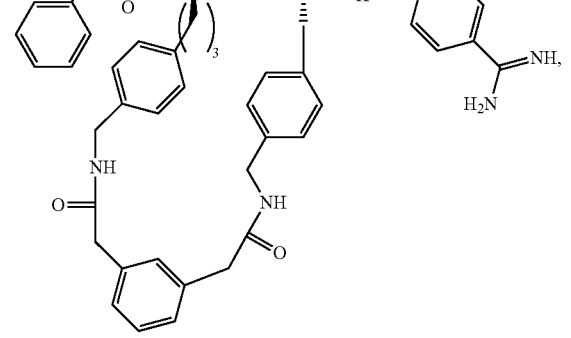

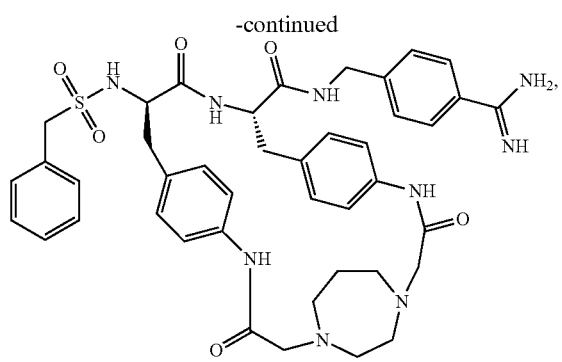
or a pharmaceutically acceptable salt thereof.
13. The compound claim 1, wherein Z-L-Z' has a structure selected from the group consisting of:
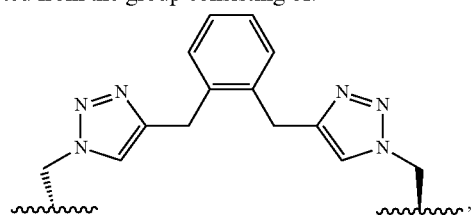
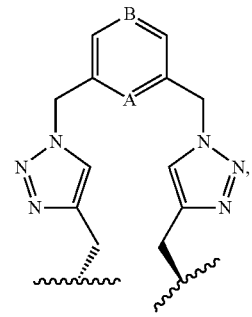
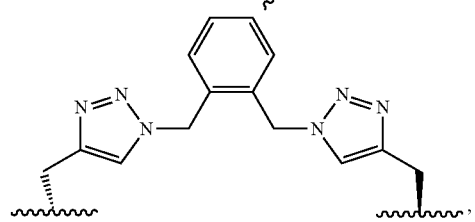
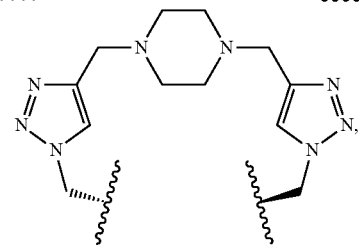
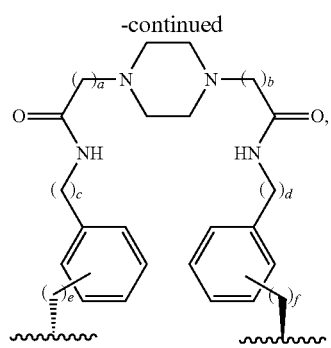
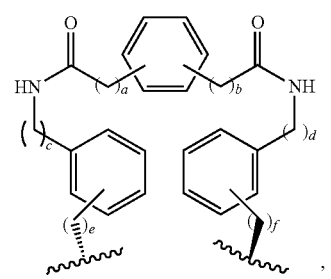
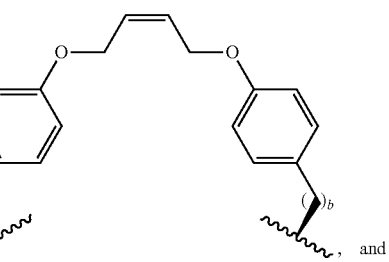, and
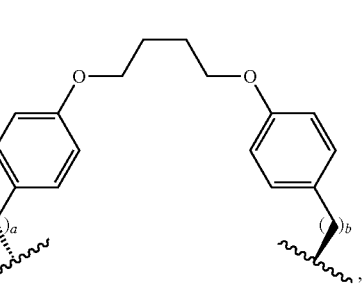,
A and B are independently CH or N; and
a, b, c, d, e, and f are independently, 0, 1, 2 or 3.
* * * * *